US012661509B2

(12) United States Patent
Kirsch et al.

(10) Patent No.: US 12,661,509 B2
(45) Date of Patent: Jun. 23, 2026

(54) TRANSCUTANEOUS ELECTRICAL NERVE STIMULATION FOR TREATING ENURESIS

(71) Applicant: Global Continence, Inc., Atlanta, GA (US)

(72) Inventors: Andrew Kirsch, Atlanta, GA (US); Ubirajara De Oliveira Barroso Júnior, Salvador (BR)

(73) Assignee: GLOBAL CONTINENCE, INC., Atlanta, GA (US)

( * ) Notice: Subject to any disclaimer, the term of this patent is extended or adjusted under 35 U.S.C. 154(b) by 236 days.

(21) Appl. No.: 18/492,422

(22) Filed: Oct. 23, 2023

(65) Prior Publication Data

US 2024/0131331 A1 Apr. 25, 2024
US 2024/0226552 A9 Jul. 11, 2024

Related U.S. Application Data

(60) Provisional application No. 63/380,465, filed on Oct. 21, 2022.

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01); *A61N 1/0492* (2013.01); *A61N 1/36007* (2013.01)

(58) Field of Classification Search
CPC . A61N 1/36034; A61N 1/0456; A61N 1/0492
(Continued)

(56) References Cited

U.S. PATENT DOCUMENTS 8,260,439 B2 9/2012 Diubaldi et al.
10,035,016 B2 7/2018 Kolb et al.
(Continued)

FOREIGN PATENT DOCUMENTS

WO WO-2020033883 A1 * 2/2020 .......... A61N 1/0492

OTHER PUBLICATIONS

International Application No. PCT/US2023/035728, International Search Report and Written Opinion, Mailed on Jan. 31, 2024, 12 pages.
(Continued)

*Primary Examiner* — Nadia A Mahmood
(74) *Attorney, Agent, or Firm* — Kilpatrick Townsend & Stockton LLP

(57) ABSTRACT

The present disclosure relates to neuromodulation, and in particular to devices and techniques for delivering non-invasive neurostimulation to treat enuresis. Particularly, aspects of the present disclosure are directed to medical device comprising a transcutaneous electrical nerve stimulation (TENS) device comprising an electronics module comprising: a controller configured to provide a set of stimulation parameters, and a pulse generator configured to generate neural stimulation based on the set of stimulation parameters. The medical device also includes one or more electrodes connected to the TENS device for delivering the neural stimulation generated by the pulse generator to a perineal region of a user, one or more gel pads for adhering the electrodes to the perineal region of the user, one or more sensors for detecting a triggering event for the neural stimulation, and a pad attached to the TENS device, the electrodes, the sensors, and the gel pads.

19 Claims, 20 Drawing Sheets

(58) Field of Classification Search
USPC ........................................................ 607/41
See application file for complete search history.

(56)                    References Cited

U.S. PATENT DOCUMENTS

| 10,463,854 B2 | 11/2019 | Perez |
| 2017/0021172 A1 | 1/2017 | Perez et al. |
| 2019/0160284 A1 | 5/2019 | Kang |

OTHER PUBLICATIONS

U.S. Appl. No. 29/951,121, "Non-Final Office Action", Nov. 26, 2025, 8 pages.
Canadian Application No. CA236668, "Office Action", mailed Sep. 5, 2025, 3 pages.
Canadian Application No. CA247354, "Office Action", Jan. 18, 2026, 2 pages.
Canadian Application No. CA247355, "Office Action", Jan. 18, 2026, 2 pages.
Canadian Application No. CA247356, "Office Action", Jan. 18, 2026, 2 pages.

* cited by examiner

200

225

250

Green - Normal Status
Yellow - Enuresis Alert
Yellow (blinking) - Error Status
Orange (blinking) - Low Battery
Orange - Charging
Green (blinking) - Battery charged
Blue (blinking) - Bluetooth active
Blue - Bluetooth connected — USB charging cable port Button
ON - Hold 3s (from off)
OFF - Hold 10 s
Activate Bluetooth - Hold 3 s
(when turned on)

230        205

200

245        235        205

225

240

210        220

Front

Back

455B

455D

455E

455F

455G

455H

4551

455J

455K

455L

<u>605</u>

Detect, by a sensor embedded in a pad of a medical device, a triggering event for neural stimulation <u>610</u>

Provide, by one or more electrodes embedded in the pad of the medical device and contacting a pelvic floor region of a user, the neural stimulation to the pelvic floor region, the neural stimulation comprising a current frequency, one or more waveform parameters based on a motor threshold of the subject, and a current intensity based on an interval between bursts of the current frequency <u>615</u>

Cause, by the neural stimulation, muscular contraction of the pelvic floor region to occlude a urethra of the user and prevent urinary loss

FIG. 6

TRANSCUTANEOUS ELECTRICAL NERVE STIMULATION FOR TREATING ENURESIS

CROSS-REFERENCES TO RELATED APPLICATIONS

This application claims the benefit of U.S. Provisional Application No. 63/380,465, filed Oct. 21, 2022, which is hereby expressly incorporated in its entirety by reference for all purposes.

FIELD

The present disclosure relates to neuromodulation, and in particular to devices and techniques for delivering non-invasive neurostimulation to treat enuresis.

BACKGROUND

Enuresis is commonly associated with the inability to control muscles such as the bladder and urinary sphincter muscles. Contracting and relaxing these muscles allows an individual to control urination. For example, muscles and nerves must work together to hold urine in the bladder and then release the urine at the right time. Nerves carry messages from the bladder to the brain to let the brain know when the bladder is full. The nerves also carry messages from the brain to the bladder, telling the bladder muscles to either tighten or release. Urinary incontinence (enuresis) is the involuntary voiding of urine a certain number of times (e.g., once, twice or greater during the day (diurnal enuresis) or night (nocturnal enuresis)). The age at which children attain urinary continence varies, but most children (greater than 90%) are continent during the day by age 5. Nighttime continence takes longer to achieve, but most children (greater than 90%) are continent during the night by age 7. In primary enuresis, an individual (typically a child) has never achieved urinary continence for ≥6 months. In secondary enuresis, individuals have developed incontinence after a period of at least 6 months of urinary control (could be several years after developing urinary control). There are many known causes for enuresis including developmental age, hormonal problems, nerve problems, bladder problems, genetics, sleep problems, medications, medical conditions, and psychological problem. For example, a nerve problem might affect an individual's bladder control if the nerves that are supposed to carry messages between the brain and the bladder do not work properly.

Enuresis has been treated in the past by medication, muscle exercises, or behavioral techniques such as scheduled eating, drinking, and trips to the bathroom, positive imagery, or bladder training with an enuresis alarm. The preferred course of treatment for enuresis is bladder training because the enuresis alarm conditions the individual to inhibit the contraction of the bladder, which ultimately results in creating lasting connections between nerves and muscles for informing the brain that the bladder is full and contracting bladder muscles to hold the urine until the urine can be properly voided. Although bladder training is well established and used worldwide, there are several problems that prevent many individuals from achieving therapeutic success. These problems include individuals who take weeks to be conditioned and during the training period the individuals continue to urinate, which causes many of the individuals to abandon bladder training. In addition, family members may be disrupted by the bladder training (e.g., woken up in the night by the alarm), which predisposes the family to stress and conflicts. While new types of diapers and bed wetting alarms have improved bladder training options, there are still deficiencies including caregivers failing to hear the alarm and take the child to the bathroom, the alarm becoming inadvertently disconnected, sensors failing or activating based on sweat as compared to urine, the child not waking to the alarm, or the child being taken to the bathroom without the alarm going off (confusion of the learning process).

Recently, neuromodulation has been used to treat enuresis by sending a mild electric current to nerves in the lower back that are involved in urination. Specifically, electrical stimulation of the posterior tibial nerve and the sacral nerve has shown promise. For posterior tibial nerve stimulation (PTNS), an electrical stimulator (pulse generator) is positioned outside the body and a small electrode is inserted through the skin of the lower leg and attached to the tibial nerve. The stimulator sends pulses to the electrode, which stimulates the tibial nerve in the leg. The electrical current then affects the nerve in the lower back that controls bladder and pelvic floor function. For sacral nerve stimulation (SNS), an electrical stimulator (pulse generator) is positioned under the skin above your buttocks and a small electrode is inserted through the skin of the back and attached to the sacrum. The stimulator sends pulses to the electrode, which stimulates the sacral nerve in the back. The electrical current then affects the bladder function.

Major challenges of neuromodulation techniques, such as via PTNS or SNS, include minimizing the invasiveness of the neurostimulation device and ensuring that optimal stimulation parameters are identified that maximally treat enuresis while minimizing or avoiding inadvertent side effects and patient discomfort. Therefore, the ability to stimulate nerves in a non-invasive manner, is important for the success of neurostimulation being used to treat enuresis. Furthermore, optimizing neural stimulation parameters and identifying the subset of parameters that may cause pain or inadvertent side effects is important from a safety perspective. Accordingly, the need exists for neuromodulation systems and techniques that are non-invasive and have the capability to optimize neuromodulation stimulation parameters.

BRIEF SUMMARY

In various embodiments, a medical device is provided that comprises: a transcutaneous electrical nerve stimulation (TENS) device comprising an electronics module comprising: a controller configured to provide a set of stimulation parameters, and a pulse generator configured to generate neural stimulation based on the set of stimulation parameters; one or more electrodes connected to the TENS device for delivering the neural stimulation generated by the pulse generator to a perineal region of a user; one or more gel pads for adhering the one or more electrodes to the perineal region of the user; one or more sensors for detecting a triggering event for the neural stimulation; and a pad attached to the TENS device, the one or more electrodes, the one or more sensors, and the one or more gel pads.

In some embodiments, the medical device further comprises a body fixation pad attached to the pad for adhering the pad to a pubic bone region of the user.

In some embodiments, the TENS device further comprises a light indicator for indicating a status of the TENS device.

In some embodiments, the TENS device is configured to be communicatively coupled to a user device.

In some embodiments, the user device is configured to send an indication of the set of stimulation parameters to the controller.

In some embodiments, the TENS device is configured to trigger an output of an alarm at the user device based on detecting the triggering event.

In some embodiments, the triggering event is an enuresis event and the one or more sensors are humidity or moisture sensors.

In some embodiments, the stimulation parameters include a frequency, an intensity, a duration, and a waveform.

In some embodiments, the frequency is between 1500 Hz and 2500 Hz.

In some embodiments, the waveform is a Russian wave current.

In various embodiments, a computer-implemented method is provided that comprises: detecting, by a sensor embedded in a pad of a medical device, a triggering event for neural stimulation; in response to detecting the triggering event, providing, by one or more electrodes embedded in the pad of the medical device and contacting a pelvic floor region of a user, the neural stimulation to the pelvic floor region, the neural stimulation comprising a current frequency, one or more waveform parameters based on a motor threshold of the subject, and a current intensity based on an interval between bursts of the current frequency; and causing, by the neural stimulation, muscular contraction of the pelvic floor region to occlude a urethra of the user and prevent urinary loss.

In some embodiments, the one or more waveform parameters comprise a Russian wave current.

In some embodiments, the current frequency is between 1500 Hz and 2500 Hz.

In some embodiments, the computer-implemented method further involves in response to detecting the triggering event, outputting an alarm.

In some embodiments, alarm is output by a user device communicatively coupled to the medical device.

In some embodiments, the medical device comprises: a transcutaneous electrical nerve stimulation (TENS) device comprising an electronics module comprising: a controller configured to provide a set of stimulation parameters, and a pulse generator configured to generate the neural stimulation based on the set of stimulation parameters; the one or more electrodes connected to the TENS device for delivering the neural stimulation generated by the pulse generator to the pelvic floor region of the user; one or more gel pads for adhering the one or more electrodes to the pelvic floor region of the user; and the pad attached to the TENS device, the one or more electrodes, the one or more sensors, and the one or more gel pads.

In some embodiments, a computer-program product is provided that is tangibly embodied in a non-transitory machine-readable storage medium and that includes instructions configured to cause one or more data processors to perform part or all of one or more methods or processes disclosed herein.

In some embodiments, a system is provided that includes one or more data processors and a non-transitory computer readable storage medium containing instructions which, when executed on the one or more data processors, cause the one or more data processors to perform part or all of one or more methods or processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present invention will be better understood in view of the following non-limiting figures, in which:

FIG. 6 shows an exemplary flowchart of providing neurostimulation in accordance with various embodiments.

DETAILED DESCRIPTION

Figure 1:
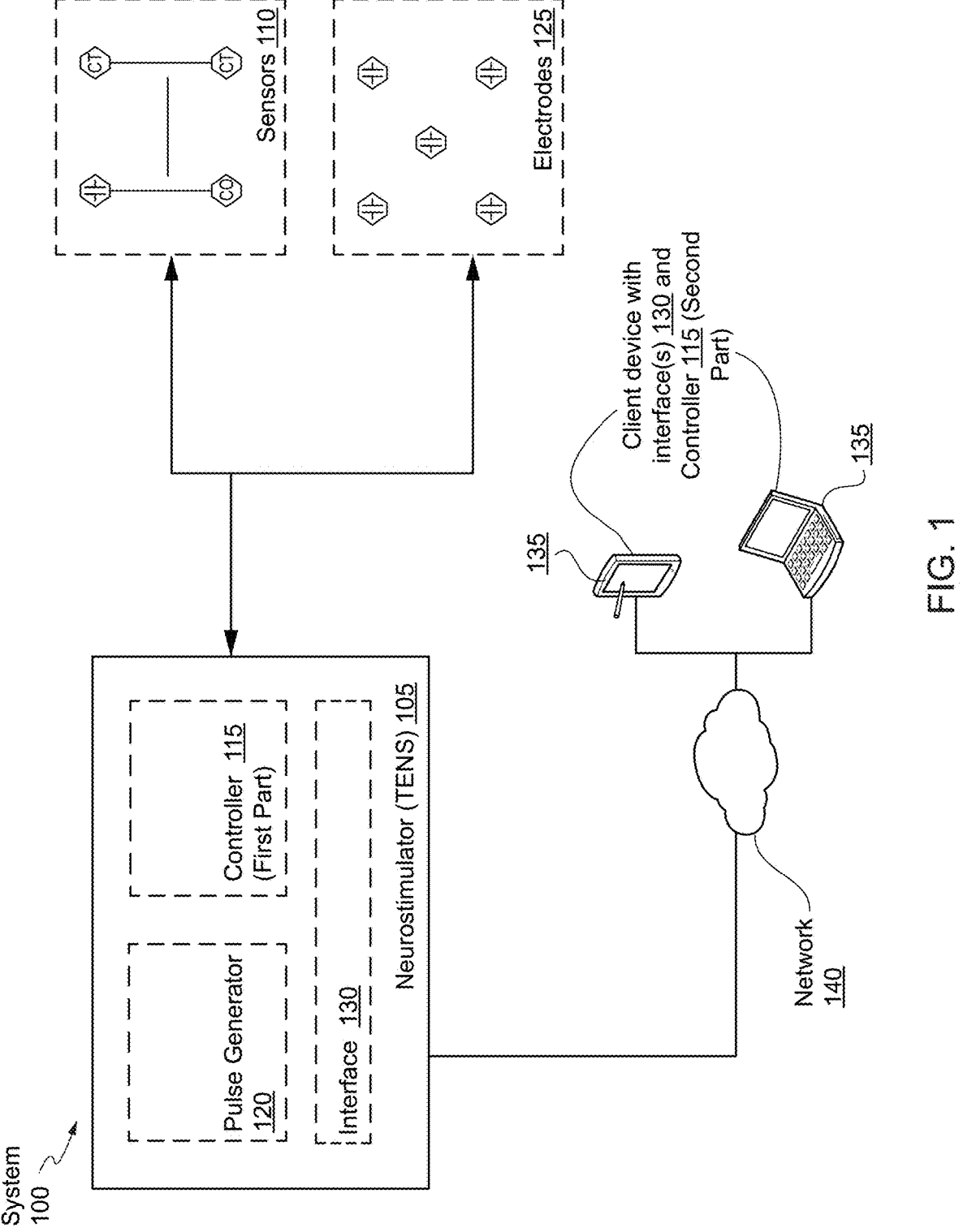
FIG. 1 shows a block diagram of a neuromodulation system in accordance with various embodiments.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed but could have additional steps not included in a figure. A process may correspond to a method, a function, a procedure, a subroutine, a subprogram, etc. When a process corresponds to a function, its termination may correspond to a return of the function to the calling function or the main function.

I. Introduction

The following disclosure describes devices and techniques for delivering non-invasive neurostimulation to treat enuresis. Various embodiments of systems and/or methods described herein may be directed toward controlling, adjusting, modifying, and/or varying one or more non-invasive manners in which neural stimulation may be applied or delivered to a patient, thereby possibly 1) influencing, affecting, maintaining, or improving neural stimulation efficacy; and/or 2) influencing, affecting, maintaining, improving, minimizing, or preventing physiological effects such as discomfort caused by the neural stimulation. As used herein, neuromodulation means the alteration of nerve activity through targeted delivery of a stimulus, such as electrical stimulation, to specific neurological sites in the body. A neurostimulator is a device or system having electronic circuit components and/or software configured to deliver the stimulus to the specific neurological site (e.g., the urethral sphincter muscles) via an electrode assembly. In accordance with various aspects discussed herein, the neurostimulator may be a transcutaneous electrical nerve stimulation (TENS) device.

TENS devices are commonly employed to administer electrical currents to specific areas of the human body, aiming to alleviate both acute and chronic pain. This stimulation involves applying electrical signals, defined by parameters such as frequency, intensity, duration, and waveform. Neural stimulation is usually administered following a treatment protocol that prescribes the most effective parameters for addressing patient symptoms. Two frequency types exist: high-frequency stimulation (above 50 Hz) causing muscle contraction and low-frequency stimulation (below 20 Hz) inducing an autonomic effect without muscle contraction. Notably, higher frequency and increased current intensity can stimulate muscle contraction.

The Russian type of current can induce muscle contraction even with low intensity. While not traditionally used for enuresis management, recent evidence suggests TENS could be considered as a supplementary or primary treatment option. Conventionally, high-frequency stimulation with sensory intensity below motor contraction is considered effective for enuresis management, enabling users to sense a full bladder or urination event. However, this requires professional calibration to ascertain the sensory threshold.

To overcome this challenge and others, a neuromodulation device or system uses medium to high-frequency stimulation (equal to or above 1500 Hz) with an intensity inducing muscle contraction. This unconventional approach overcomes the need for professional calibration, consistently reaching a motor threshold without activating the sensory nerve threshold. The device features several predefined electrical stimulation levels (e.g., 1-7), each with varying intensity. The selected level is the lowest one achieving a motor threshold, causing visible muscle contractions. Users start with the lowest setting, increasing it if moisture (e.g., urine) is detected after electrical stimulation. This process repeats until muscle contractions sufficient to halt enuresis are achieved. Thus, the neuromodulation device consistently attains the motor threshold without requiring professional calibration and avoids reaching the sensory nerve threshold.

Additionally, to achieve a motor threshold without reaching a sensory nerve threshold, the neuromodulation device or system can use a Russian wave current rather than a square wave. This is because the Russian wave current can induce muscle contraction even with low intensity. Furthermore, the neuromodulation device or system can use a frequency greater than 2000 Hz. Regarding the intensity of the current, the neuromodulation device or system is regulated by the interval between bursts, rather than an amperage level. The current may be modulated at 50 bursts per second with a phase duration of 400 μs. The wave, the frequency, and how the intensity of current is regulated can be modified based on an application of the neuromodulation device or system. The neuromodulation device or system can also include electrodes that allow conduction of electric current to the skin that are superficial and placed in a perineal region of an end user.

A sensor of the neuromodulation device can detect moisture or humidity and then stimulate the electrodes to cause the perineal musculature to contract, occluding the urethra, while simultaneously inhibiting the contraction of the bladder by reflex. As a result, urinary loss is prevented while the individual is sleeping. The neuromodulation device can have an electrical stimulation of the innervation of the perineal musculature causing a contraction of the external urethral sphincter. This contraction can cause immediate interruption of the urinary flow, avoiding the loss of urine. The neuromodulation device can eliminate a need to increase the intensity of the stimulation until the end user feels discomfort, which can lead the end user to give up the method for fear that they might feel the discomfort again during the enuresis episode. Aspects of the present disclosure provide the neuromodulation device that does not reach a sensing threshold previously calibrated by a professional.

One advantage of this method is that the end user effectively will not urinate once the neuromodulation device is utilized; the brain is then temporally "taught" when the bladder contracts. The contraction of the perineal musculature by the neuromodulation device causes a brain stimulation by the pelvic innervation that reaches superior nerve centers. Over time, the end user becomes conditioned and self-controls urination, unconsciously. Thus, the neuromodulation device prevents nighttime incontinence in concurrence with brain conditioning.

In various embodiments, the neuromodulation system or device may further include or trigger an alarm system and/or a vibration mechanism. The alarm and vibration may be triggered along with the electrical stimulation of the electrodes. The vibration adds more stimulus to the end user, so they are warned when leakage occurs. Since the electrical stimulation is the main mechanism of action, the auditory (e.g., beep) and vibratory stimuli may be turned off at the discretion of the user.

The neuromodulation device may be coupled to a pad that is disposable, and the sensor and the electrodes can be printed or fixed thereon. The neuromodulation device can include a non-disposable template that houses the sensor and contacts a TENS device and the electrodes. Therefore, wires may be minimized or eliminated in the neuromodulation system. In addition, the neuromodulation device may be rechargeable and operate by Bluetooth, Wi-Fi control, or other suitable method of wireless connection. As a result, the neuromodulation device can be controlled independent of its use (e.g., remotely). The neuromodulation device may additionally be able to work offline. In some instances, the neuromodulation device can be communicatively coupled to a mobile device of a user, and the mobile device may be used to modify the settings of the neuromodulation device. For instance, the user may use the mobile device to increase or decrease the intensity of the current and turn on and off the alarm or the vibration of the neuromodulation device. The alarm may come from the neuromodulation device itself, or the alarm may come from one or more mobile devices. For example, the neuromodulation device may wirelessly transmit (e.g., via Bluetooth, Wi-Fi, or the like) a signal to the one or more mobile devices to trigger an alarm at the one or mobile device. As such, unnecessary personnel in proximity to the end user may not be woken up when the neuromodulation device is activated. Or, a caregiver of a child wearing the neuromodulation device may be notified when the neuromodulation device is activated. In addition, the time of the events (e.g., day and time when the neuromodulation device is activated) can be recorded by the neuromodulation device.

The neuromodulation system of the present disclosure has several advantages. For instance, since the neuromodulation device can be operated by Bluetooth, Wi-Fi, or the like, a risk of the user manipulating (e.g., turning off) the neuromodulation device while they sleep can be decreased. This can increase the efficacy of the neuromodulation device and safety for end users. In addition, the neuromodulation device can communicate with a mobile application on a user device to provide an interface for user interaction with the neuromodulation device. Furthermore, the neuromodulation device can allow a professional to follow the evolution of the end user's treatment. Additionally, the neuromodulation device can signal a mobile phone of the patient and/or caretaker at the exact moment of the enuresis, thus preventing inadvertent awakening of other family members.

One illustrative example of the neuromodulation device includes a portable electronic device capable of detecting the presence of urine by means of a humidity sensor and generating an electrical signal. An LED light indicates the activation state. The electrical signal can last for a predetermined amount of time. The LED light may remain on until the neuromodulation device is turned off. The neuromodulation device may perform one cycle of electrical stimulation before needing to be set up again prior to another usage.

Another illustrative embodiment of the present disclosure comprises a neuromodulation system with a TENS device having an electronics module that includes a controller configured to provide a set of stimulation parameters, and a pulse generator configured to generate neural stimulation based on the set of stimulation parameters. The neuromodulation system also includes one or more electrodes connected to the TENS device for delivering the neural stimulation generated by the pulse generator to a perineal region of a user. The neuromodulation system also includes one or more gel pads for adhering the one or more electrodes to the perineal region of the user. The neuromodulation system also includes one or more sensors for detecting a triggering event for the neural stimulation and a pad attached to the TENS device, the one or more electrodes, the one or more sensors, and the one or more gel pads.

Advantageously, these approaches provide neuromodulation devices and systems that are non-invasive and capable of detecting and/or tracking effects due to neuromodulation therapy and closing the loop on stimulation parameters. For example, the neuromodulation devices or systems described herein can adjust stimulation parameters to emit a signal, which causes muscle contraction without reaching a sensitivity threshold of the user. So, the neuromodulation devices can be operated autonomously without calibration to the user by a healthcare professional.

II. Neuromodulation Devices or Systems

FIG. 1 shows a neuromodulation system 100 in accordance with some aspects. In some embodiments, the neuromodulation system 100 includes a neurostimulator 105, optionally one or more sensors 110, and a controller 115. The neurostimulator 105 includes software and/or electronic circuit components such as a pulse generator 120 that generates an electrical signal to deliver electrical stimulation to a nerve. In certain embodiments, the neurostimulator 105 is a TENS device that is integrated or attached to or pad worn by a patient at a location remote from or near to the nerve and is configured to deliver the signal to the nerve via one or more electrodes 125. The pad may be structured to position the one or more electrodes 125 in the perineal region, sacral region, or in other locations of the patient's body depending on a particular treatment. For example, the neuromodulation system 100 may be used to treat nocturnal enuresis by stimulation of the pelvic floor at the time of the enuresis event or treat stress incontinence by contraction of the pelvic floor at the time of the enuresis event. For at least some treatments, the neuromodulation system 100 may be used to strengthen the perineal or perivaginal muscles of the end user by means of contractions. For at least some treatments, the stimulation of the innervation of the perineal or perivaginal muscles may be used to cause contraction of the external urethral sphincter. At least some of the treatments may involve causing cerebral stimulation by the pelvic innervation that goes through the medulla to higher nerve centers, and may cause neuroplasticity. At least some of the treatments may result in conditioning a user to control urination and/or defecation on their own during the day. At least some of the treatments may result in conditioning the user to control urination and/or defecation on their own during sleep (day or night). At least some of the treatments may result in preventing urinary incontinence or defecation while the cerebral conditioning is occurring. In some embodiments, the one or more electrodes 125 are exposed on a surface of the pad such that the one or more electrodes 125 are placed in contact with the end user's skin in the region selected depending on the treatment.

The one or more sensors 110 may include software and/or electronic circuit components that sense moisture or humidity. Additionally or alternatively, the one or more sensors 110 may include software and/or electronic circuit components that sense nerve responses to the stimulation. The nerve responses may include muscle contractions, enuresis-based parameter changes (e.g., preventing the flow of urine or allowing the flow of urine), bowel movement parameter changes (e.g., induced defecation), or a combination thereof. In certain embodiments, the one or more sensors 110 are integrated or attached to a pad worn by a patient at a location remote from or near to the nerve and are configured to receive signal(s) indicative of humidity or moisture. In some embodiments, the one or more sensors may be located at other locations external to the patient (e.g., around their leg) and/or may be placed in a cavity of the end user.

The controller 115 includes software and/or electronic circuit components that control stimulation parameters of the neurostimulator 105 and/or cause delivery of the stimulation via the neurostimulator 105 and one or more electrodes 125. In some embodiments, the controller 115 is a part of the neurostimulator 105 and is in communication with the pulse generator 120 and the one or more sensors 110 via a wired or wireless connection. In certain embodiments, the controller 115 is also part of client device(s) 135 and is in communication with the pulse generator 120 and the one or more sensors 110 via a network 140 (e.g., a wireless connection such as Bluetooth). For example, the controller 115 may have at least two parts. A first part is part of the neurostimulator 105 and is in communication with the pulse generator 120 of the neurostimulator 105 and the one or more sensors 110 via a wired or wireless connection. A second part is remote from the neurostimulator 105 (e.g., implemented as part of an external programmer or application on a client device 135 such as an end user's cell phone) and is in communication with the first part.

While the neurostimulator 105, one or more sensors 110, and controller 115 are described herein as a self-contained system integrated at least partially into a pad worn by an end user with respect to several described embodiments, it should be understood that various systems and arrangements comprising the neurostimulator 105, one or more sensors 110, and controller 115 are contemplated without departing from the spirit and scope of the present disclosure. For example, the neuromodulation system 100 may include the neurostimulator 105, one or more sensors 110, and controller 115 within a distributed environment such as a cloud computing environment, and the neurostimulator 105, one or more sensors 110, and controller 115 may be in communication via one or more communication networks 140. Examples of communication networks 140 include, without restriction, the Internet, a wide area network (WAN), a local area network (LAN), an Ethernet network, a public or private network, a wired network, a wireless network (e.g., WiFi or Bluetooth), and the like, and combinations thereof.

Figure 2A:
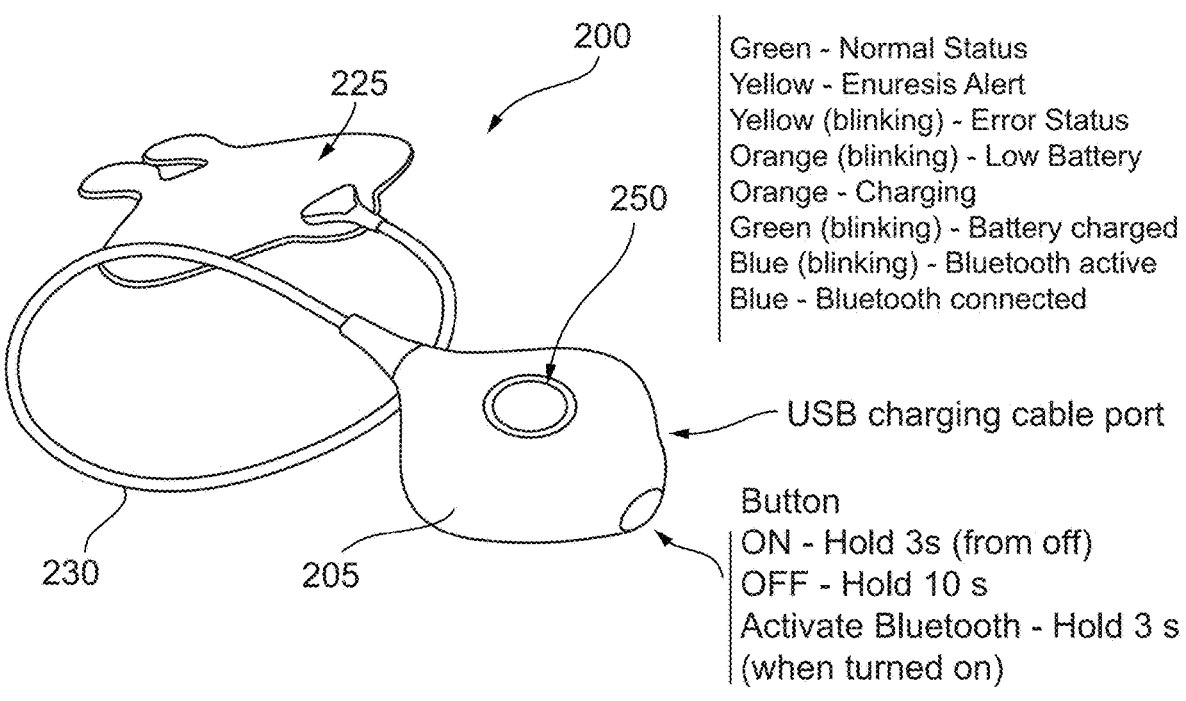
FIG. 2A shows a neuromodulation system in accordance with various embodiments.
Figure 2A:
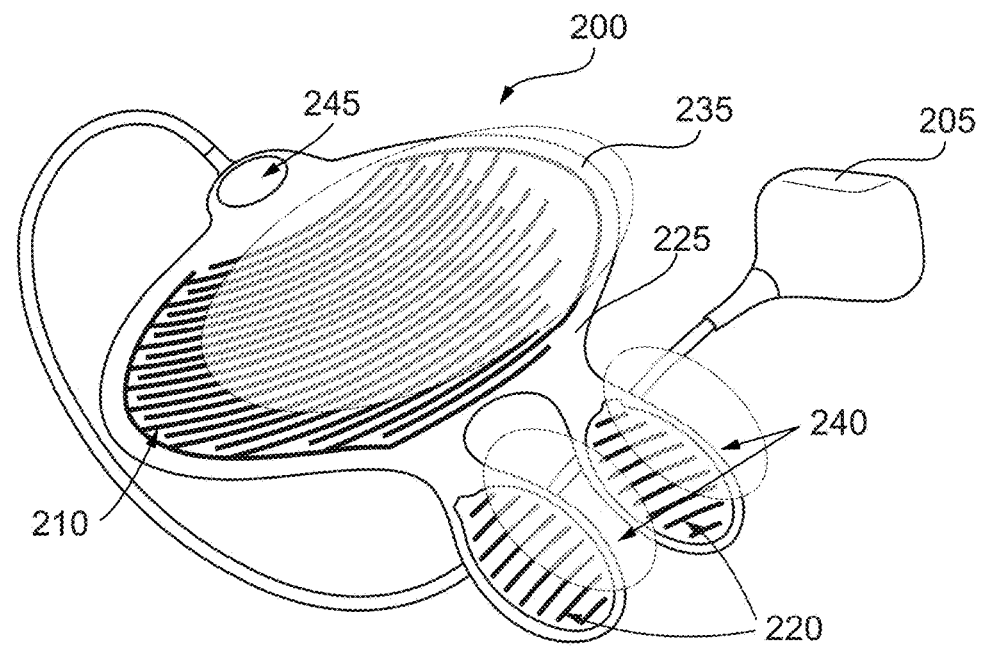
Figure 2B:
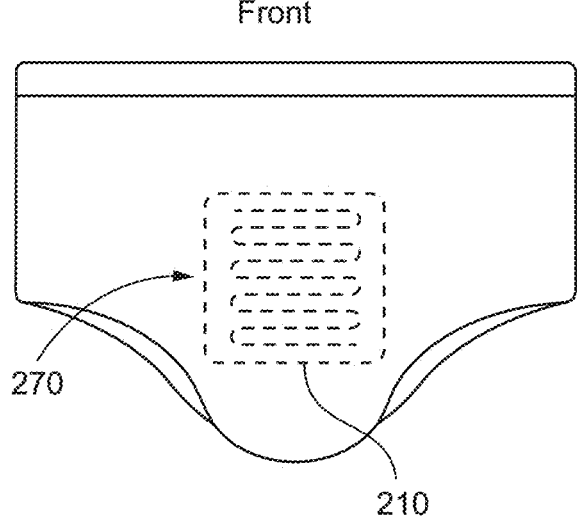
FIG. 2B shows an example of an undergarment incorporating a humidity sensor and an electrical stimulator (electrode(s)) in accordance with various embodiments.
Figure 2B:
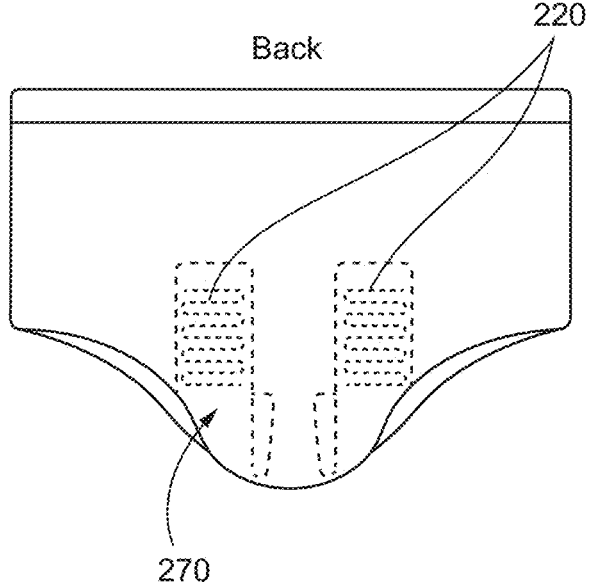

FIG. 2A shows a neuromodulation system 200 in accordance with some aspects. In various embodiments, the neuromodulation system 200 includes a neurostimulator 205 (e.g., a neurostimulator 105 as described with respect to FIG. 1), one or more sensors 210 (e.g., one or more sensors 110 as described with respect to FIG. 1), a controller (e.g., a controller 115 as described with respect to FIG. 1), and one or more electrodes 220 integrated with a pad 225 to be worn by an end user. The pad 225 may be any suitable shape or configuration. For example, the neurostimulator 205, the sensors 210 and the electrodes 220 may be embedded and fixed within the pad 225. Alternatively, the electrodes 220 and sensors 210 can be embedded and fixed within an undergarment (e.g., undergarment 270 in FIG. 2B). Therefore, the hardware needed for treatment may be concealed by the pad 225 or the undergarment 270. In certain embodiments, some or all of the hardware may be printed on or otherwise incorporated into a flexible plastic construct (e.g., polyimide with an overmold of silicon) that is housed in the pad 225 or undergarment 270-. The neurostimulator 205, the sensors 210, controller, and the electrodes 220 are in wired 230 or wireless communication with one another to implement the operations described in further detail herein.

Figure 2C:
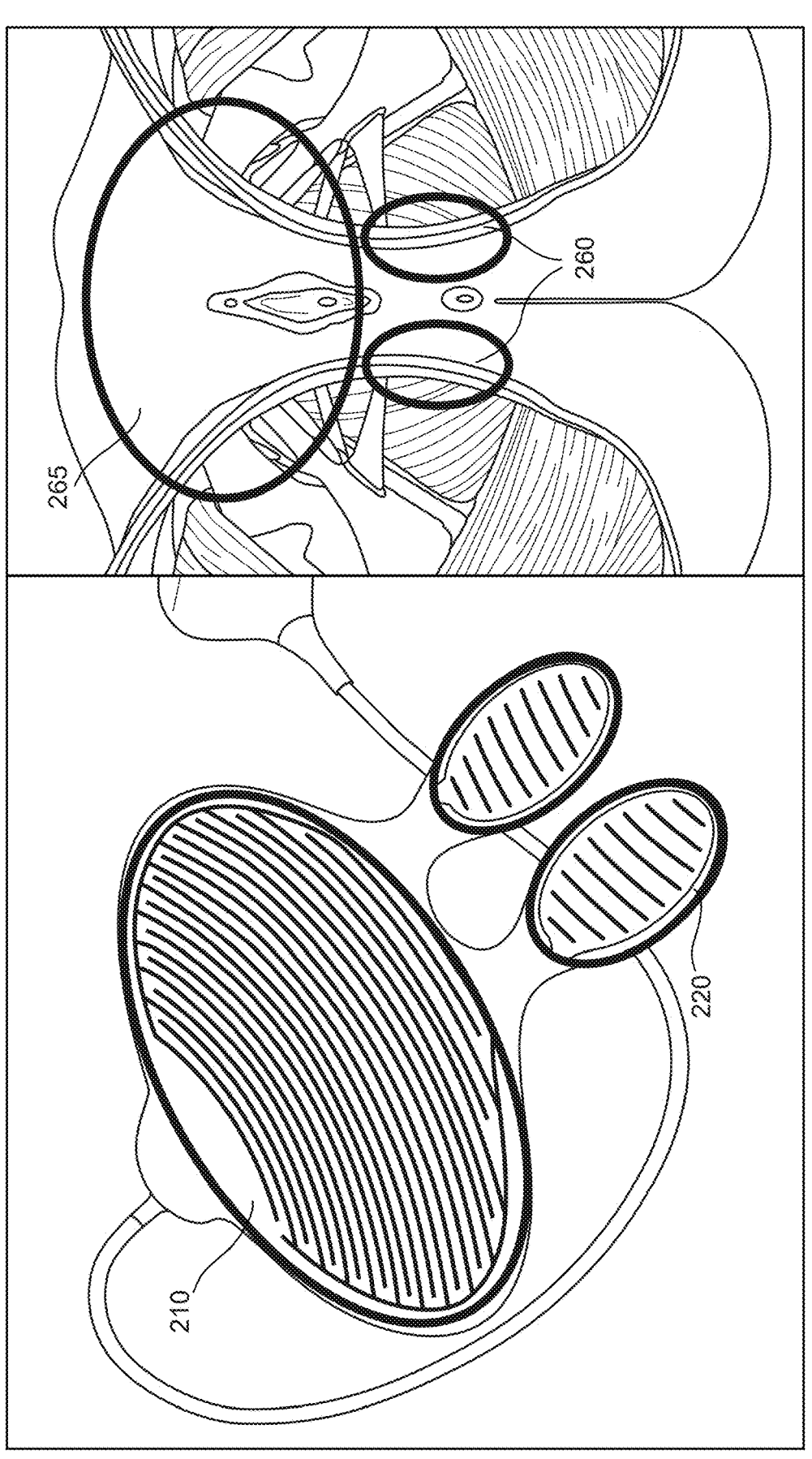
FIGS. 2C and 2D show the nerves associated with a neuromodulation system in accordance with various embodiments.
Figure 2D:
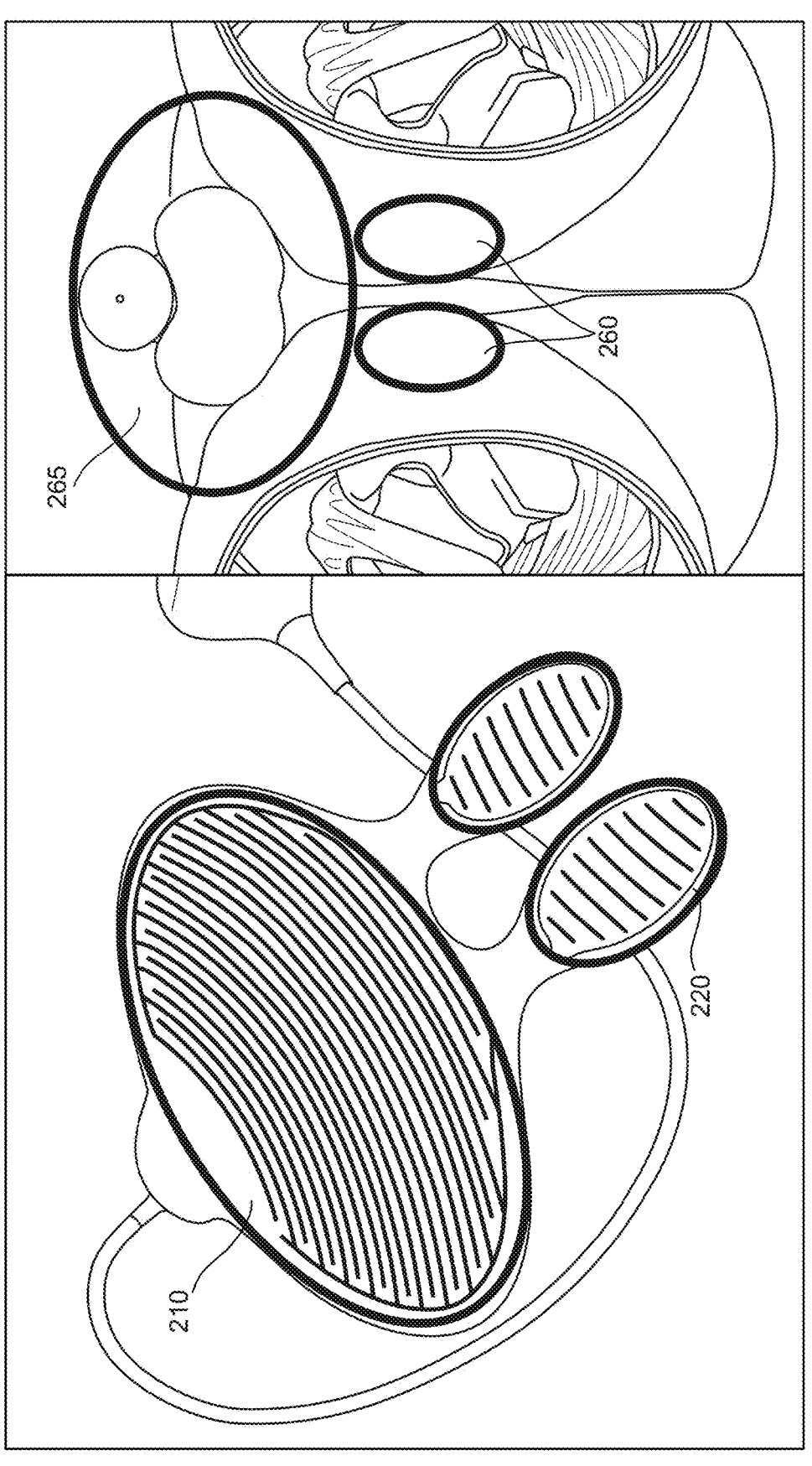

In some instances, the sensors 210 comprise a moisture or humidity sensor to measure the release of urine or wetting of the pad 225. The neuromodulation system 200 also includes an absorbent pad 235, one or more gel pads 240, and one or more body fixation pads 245. The absorbent pad 235 can be positioned over the sensors 210 so that the sensors 210 are not in direct contact with the end user's skin. The absorbent pad 235, gel pads 240, and body fixation pads 245 can be disposable. The one or more gel pads 240 and the one or more body fixation pads 245 can adhere the pad 225 to the end user's skin in various regions. For example, the one or more gel pads 240 may be placed over the electrodes 220 and may adhere to a first region of the end user's body (e.g., the perineal region 260 in FIGS. 2C-2D). In addition, the body fixation pads 245 can be attached to an area of the pad 225 that is placed in another region of the end user's body (e.g., pubic bone region 265 in FIGS. 2C-2D) so that the body fixation pads 245 adhere the pad 225 to that region of the end user's body. Placement of the sensors 210 and electrodes 220 with respect to the end user is illustrated in FIGS. 2C-2D.

The pad 225 may be structured to position the electrode(s) 220 in or near a region of the end user's body (e.g., the sacral region or an intracavitary region) depending on the particular treatment. In some instances, the electrodes 220 are positioned on an inside surface of the pad 225, as shown in FIG. 2A. In some embodiments, the electrodes 220 are placed in an area of the pad 225 that is midline, bilaterally, or unilaterally in the distribution of a target region such as the urethral sphincter muscles. In other embodiments (for the same or other treatment), other muscles or nerves may be targeted for stimulation. The pad 225 may be fabricated of various types of fabric or polymers such as cotton, linen, polyester, polyurethane, polyimide, silicone, or the like and various combinations thereof, and the electrodes 220 (electrical stimulators) may be attached to pad 225 in a various manners such as snaps or adhesive. The electrodes 220 may be formed of a conductive material such as a copper, silver, gold, platinum, stainless steel, nickel-cobalt base alloy, platinum-iridium alloy, brass, bronze, aluminum, etc., and take the form of probe electrodes, linear electrodes, paddle electrodes, pad electrodes, and the like, for example. The electrodes 220 may be any size or any shape, as well as disposable or reusable.

The neurostimulator 205 may be a TENS device having a housing, a power source, an antenna, an electronics module (e.g., a computing system), and an indicator 250, such as a light emitting diode (LED), alarm, or interface notice. The housing may be comprised of materials that are biocompatible such as bioplastics, bioceramics or bioglasses for radio frequency transparency, metals such as aluminum or titanium, and/or plastics such as polyimide or polyurethane. In accordance with some aspects, the size and shape of the housing are selected such that the neurostimulator 205 can be integrated with the pad 225. The power source may be within the housing and connected (e.g., electrically connected) to the electronics module to power and operate the components of the electronics module. In some embodiments, the power source is rechargeable. The power source (e.g., an internal battery) of the neurostimulator 205 may be rechargeable. The antenna may be connected (e.g., electrically connected) to the electronics module for wireless communication with external devices. The electronics module may be connected (e.g., electrically connected) to wires 230 that terminate at the sensors 210, electrodes 220, and optionally a ground such that the electronics module is able to receive a signal from the sensors 210 or apply a signal or electrical current to electrodes 220. The indicator 250 may have different settings based on a status of the neurostimulator 205. For instance, an alarm may be in the neurostimulator 205 and/or in another pre-established communication device such as an external programmer 280 (e.g., an external computing device of an end user or a care giver). The neurostimulator 205 may additionally include a vibration mechanism for providing vibration stimuli to the end user in response to the sensors 210 detecting moisture.

In various embodiments, the electronics module 260 is a printed circuit board in combination with discrete and/or integrated electronic circuit components such as application specific integrated circuits (ASICs). In some embodiments, the electronics module 260 can be remotely accessed through the external programmer 280. In some embodiments, the external programmer 280 may comprise at least a portion of the controller 215. For example, the external programmer 280 can be used by the end user or a healthcare professional to: (i) turn on and off the neurostimulator 105, (ii) check and program the electronics module 260 via an interface after deployment with an end user, and (iii) input or adjust stimulation parameters via an interface during a stimulation process, e.g., providing an initial set of the stimulation parameters. The external programmer 280 may communicate with the electronics module 260 via wired or wireless communication methods, such as, e.g., wireless transmission. Since wireless communication such as Bluetooth permits a device devoid of an interface, this configuration may increase safety of the TENS device by not allowing an end user such as a child to purposefully manipulate the TENS device or inadvertently manipulate the TENS device while they sleep. However, it should be understood that an interface on the TENS device may be optional for when external programming (e.g., Bluetooth) is not utilized. The interface on the TENS device may be configured to allow the same functionality provided via the external programmer 280. Moreover, wireless functionality may be used to send alerts to the external programmer 280 or computing device (e.g., a caregiver's cell phone) in response to enuresis events or other detected or occurring events.

Upon the sensors 210 detecting urine, the sensors 210 can activate the electrodes 220 to deliver an electric current-based functional electrical stimulation (FES) to contract the urethral sphincter and assist in stopping urination. The neurostimulator 205 may be programmed for one cycle totaling five seconds on, of which contains one second of rise, three seconds of sustaining, and one second of decay. The neurostimulator 205 may initially be used at a lowest electrical stimulation level (e.g., Level 1). If the user continues to experience enuresis, the stimulation level can be increased periodically (e.g., nightly by one level up to level 7). The stimulation level may be raised incrementally until the maximum level. A lower level may be restored if the stimulus becomes uncomfortable for the user.

III. Electric Components for Delivering Neuromodulation

Figure 3:
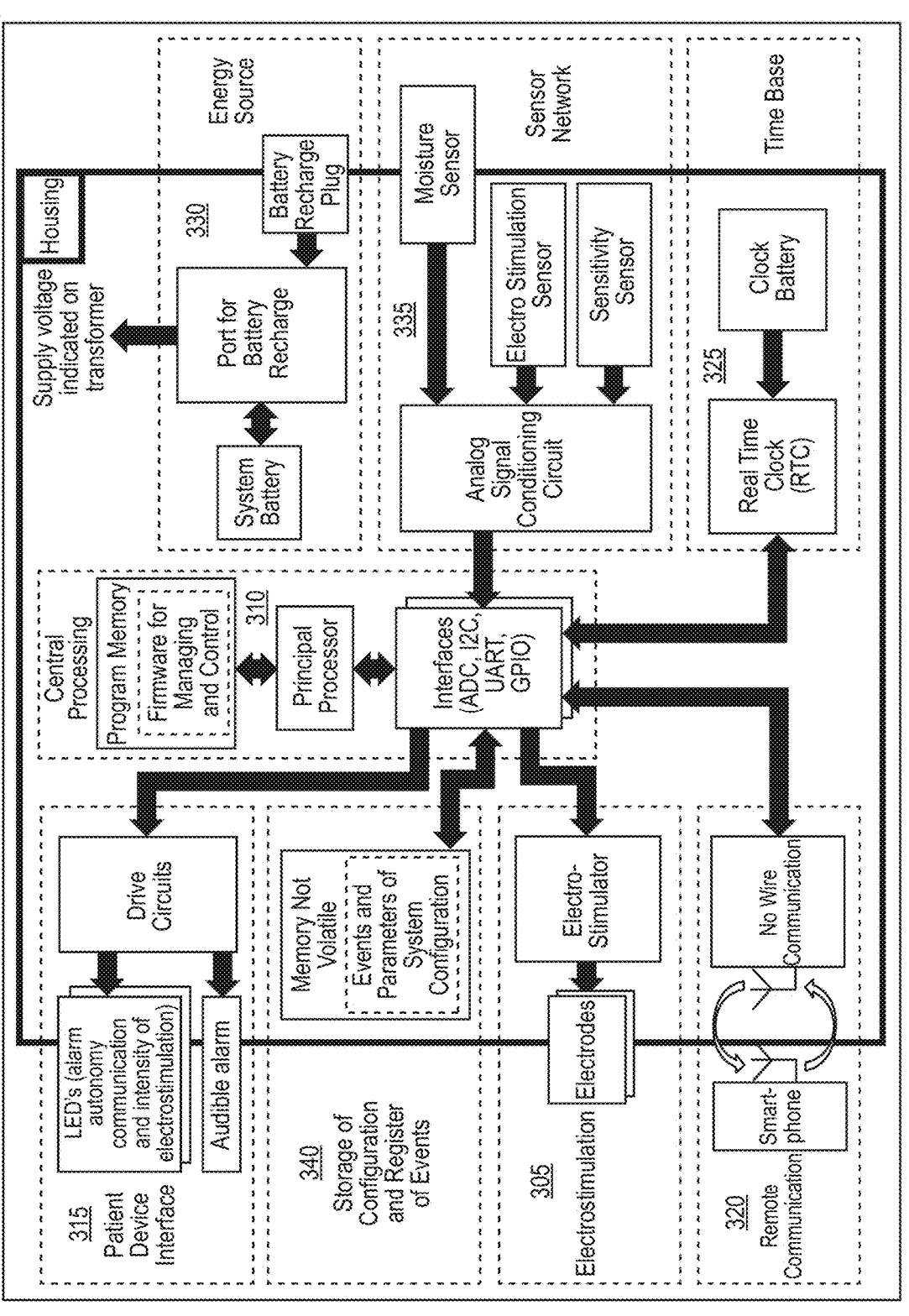
FIG. 3 shows a block diagram of an electronics module in accordance with various embodiments.

FIG. 3C illustrates an electronics module 300 that includes discrete and/or integrated electronic circuit components that implement analog and/or digital circuits capable of producing the functions attributed to the neuromodulation devices or systems described herein. In some instances, the electronics module 300 includes an electrostimulator or pulse generator 305 that generates a signal to deliver stimulation to a muscle via the one or more electrodes, at least a portion of the controller 310 that comprises one or more processors and interfaces, drive circuits 315 for interfaces and driving indicators such as LEDs, interface notices, or alarms, a communications module 320 for wired or wireless communication, a clock module 325 that maintains real time for processing, battery life, and time stamps, a battery module 330 for maintaining state of the power source, signaling circuitry 335 for receiving feedback from the one or more sensors, and a memory 340 with program instructions operable on by the pulse generator 305 and the controller 310 to perform one or more processes described herein.

The pulse generator 305 may be configured to set or adjust one or more stimulation parameters based on commands from the controller 310. Examples of stimulation parameters include frequency, intensity, duration, and waveform. In some embodiments, neural stimulation is delivered via the pulse generator 305 in a stimulation burst, which is a train of stimulation pulses programmed with any combination of frequency, intensity, duration, and waveform. Stimulation bursts can be characterized by burst durations and burst intervals. Burst duration is the length of time that a burst lasts. Burst interval can be identified by the time between the start of successive bursts. The pattern of bursts can include any combination of burst durations and burst intervals. A simple burst pattern with one burst duration and burst interval can continue periodically for a programmed period or can follow a more complicated schedule. The programmed pattern of bursts can be composed of multiple burst durations and burst interval sequences. The programmed pattern of bursts can be characterized by a duty cycle, which refers to a repeating cycle of neural stimulation ON for a fixed time and neural stimulation OFF for a fixed time. Stimulation intensity can be determined by the interval between bursts. Larger intervals can be associated with greater intensities.

Pulse frequency of the electrical current may be classified as high frequency (>50 Hz), low frequency (<10 Hz), and burst (bursts of high frequency current applied at a much lower frequency). In various instances, the frequency may be adjusted between 1500 Hz and 2500 Hz. Pulse duration is the interval between the time, during the first transition, that the amplitude of the pulse reaches a specified fraction of its final amplitude, and the time the pulse amplitude drops, on the last transition, to the same level. In some instances, the pulse duration (or width) may be varied from about 40 to 1000 micro seconds (μs), for example between about 40 and about 250 μs or between about 450 and about 850 μs. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

There are different waveforms that may be used in the neurostimulation and these waveforms perform differently and have varied treatment attributes. The various waveforms used in the neurostimulation may be designed to target specific areas of the body and to provide customized forms of energy transfer. This variance in energy transfer helps address diverse therapy needs, e.g., enuresis, sexual dysfunction, pain, etc. The waveform signal may vary from monophasic current (unidirectional) or biphasic current (bidirectional) and have several formats, with variable repetition rates (frequency) from 1500 Hz to 2500 Hz, variable pulse widths (duration) from 100 to 1000 μs, with an adjustable current intensity between 0 mA to approximately 35 mA. Monophasic current refers to a single phase, or pulse, of intensity followed by a period of rest. This type of stimulation is typically used in pain management but may be used to generate a motor response. Biphasic current refers to two phases, or pulses, of two different intensities alternating with each other during treatment. Biphasic current is considered the most versatile of the stimulation therapy waveforms because the amplitude (intensity), stimulation (voltage), current, and duration may be controlled for each phase or pulse. With its versatility and effectiveness, biphasic current stimulation can be used to strengthen muscles, muscular re-education, increase circulation, and decrease swelling.

These parameters can be adjusted automatically by the controller 310 or by any suitable wired or wireless apparatus via communications module 320. In some instances, the generated waveforms may be based on Russian current waveforms, square waveforms, bell-shaped waveforms, or other waveforms not previously employed for the enuresis. For example, the Russian current waveform is a type of electrical stimulation that delivers medium frequency current in alternating pulses or bursts of energy. This type of stimulation generates a motor response which can be used to strengthen muscles and muscular re-education. Consequently, this type of stimulation can be used such that the neuromodulation device or system does not need calibration by a professional because the neuromodulation device or system will only ever reach a motor threshold (muscle end). Interferential current may be used to address chronic, post-surgical and post-trauma acute pain in patients. Premodulated current is similar in its benefits and ease of use for patients as interferential current. The main difference between the two is how the current is delivered to the patient's muscle tissue. With premodulated current, a single channel is used to mix the frequencies prior to delivery of the current through the electrode of the body (using two electrodes rather than four). This is beneficial when treating areas of the body that have less space available for electrode placement.

In various embodiments, the controller 310 includes one or more processors and interfaces to perform instructions embedded in the memory 340 to perform functions associated with the neural stimulation therapy, such as performing neural stimulation based on a stimulation schedule stored in the memory 340 and/or based on feedback received via the interfaces and/or the sensors. The controller 310 is in communication with the pulse generator 305 and the one or more sensors via the signaling circuitry 335. For example, the controller 310 may be configured to perform functions associated with the neural stimulation therapy including determining a presence of moisture above a set threshold using a moisture sensor and based on the determined presence of moisture, delivering neural stimulation using the pulse generator 305 and the one or more electrodes based on a set of stimulation parameters to a nerve.

The memory 340 may be a non-transitory machine readable storage medium having instructions stored thereon that when executed by a processor (e.g., a processor of the controller 310) causes the processor to perform one or more operations such as generation of a signal or electric current based on one or more stimulation parameters. The memory 340 may store operating records, pre-established waveforms and parameters for neurostimulation signals, sets or parameters currently being used by the controller 310, and operating instructions. In some embodiments, the operating records, pre-established waveforms and parameters for neurostimulation signals, sets or parameters currently being used by the controller 310, and operating instructions are stored in one or more data tables of the memory 340. In some embodiments, the operating records include a record of medial events (e.g., a record of each enuresis event detected by the neuromodulation system) and therapy provided in response to the medical event (e.g., the stimulation signal used with parameters). The operating records may be time stamped and may be communicated via communications module 320 to an external device such as the external programmer, a health care providers computing device, or a distributed environment system (e.g., a cloud). The operating records may be accessed by a user interacting with one or more interfaces of the neurostimulator, the external programmer, or other computing device.

In some embodiments, the memory 340 includes instructions operable on by the controller 310 to cause the on-demand stimulation therapy, receive therapy feedback and modify the therapy based on the feedback. The modification may include gradually increasing or decreasing the intensity of the neural stimulation signal to a desired or target therapeutic level. In other embodiments, the memory 340 includes instructions operable on by the controller 310 to control titration of the therapy. During the titration, the neural stimulation signal may be delivered using different combinations of stimulation parameters and the effects of the stimulation (e.g., the desired physiological effects and/or adverse physiological effects such as absence of muscle contraction or increased pain) are evaluated for the different parameter combinations to determine an optimal set or combination of stimulation parameters that provide the desired therapeutic effect while minimizing or preventing adverse physiological effects. In yet other embodiments, the memory includes instructions operable on by the controller to adjust or select a combination of stimulation parameters that is determined to be effective at generating a desired nerve response.

Figure 4A:
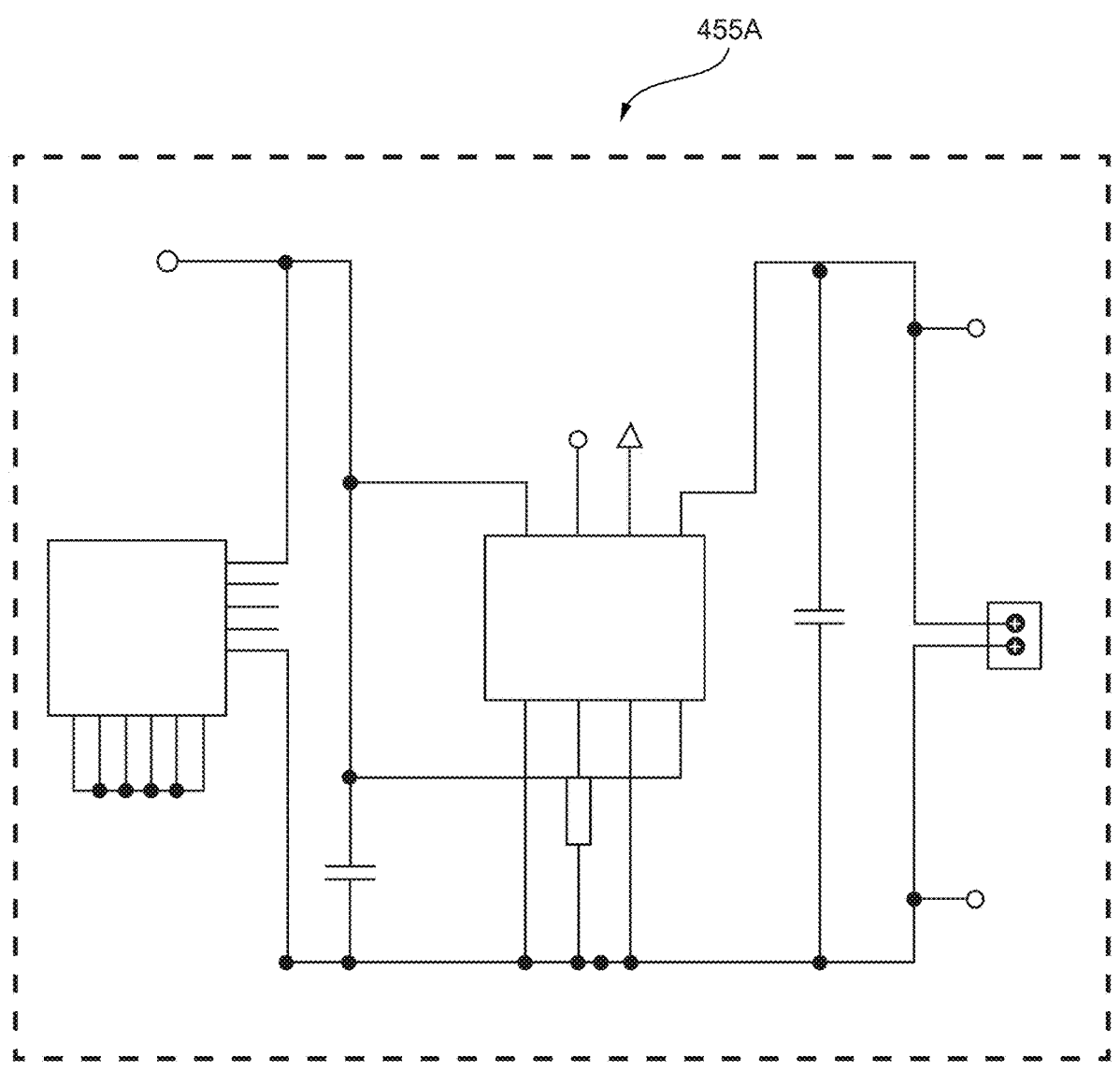
FIGS. 4A-4L show exemplary electronics components in accordance with various embodiments.
Figure 4B:
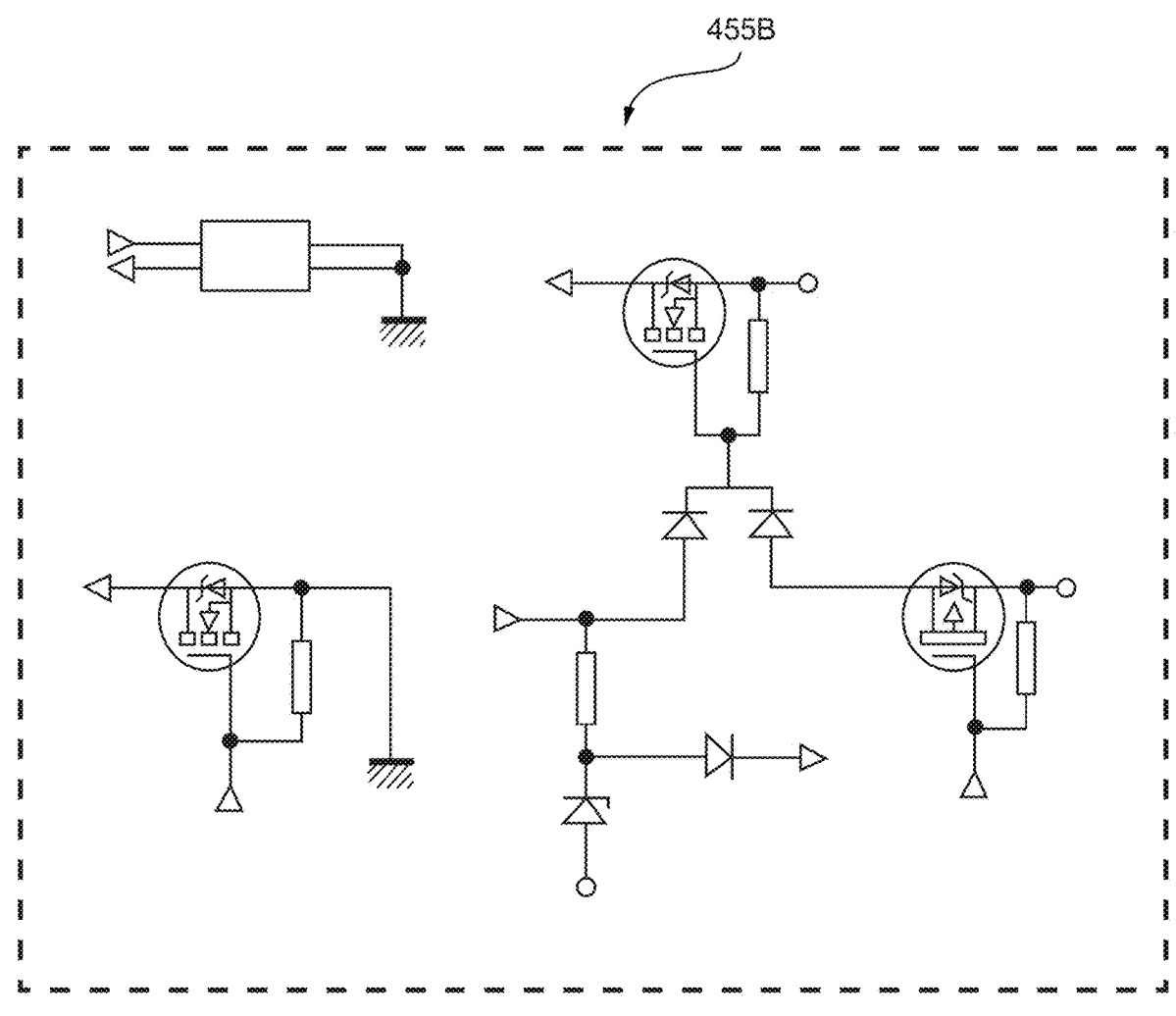
Figure 4C:
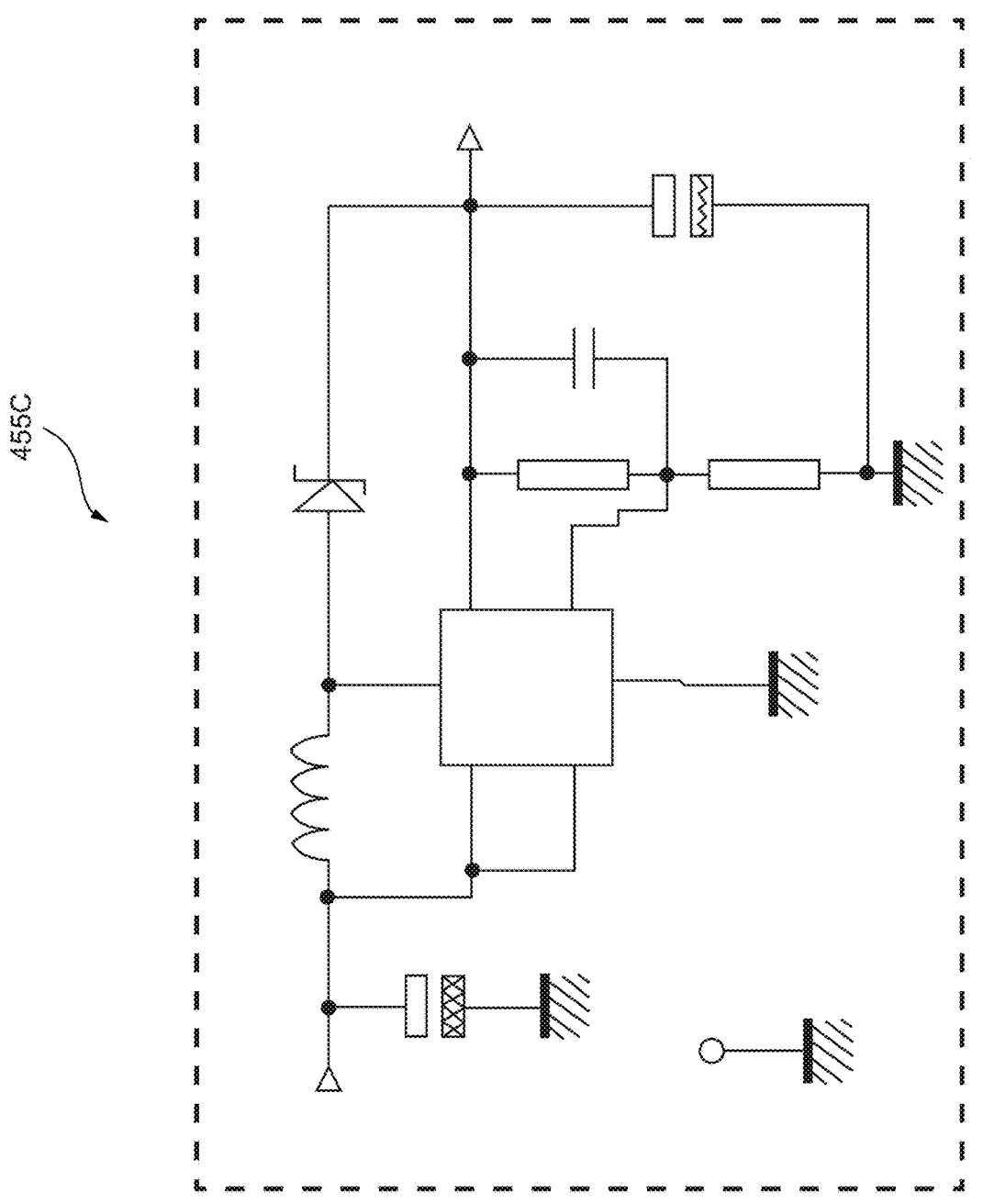
Figure 4D:
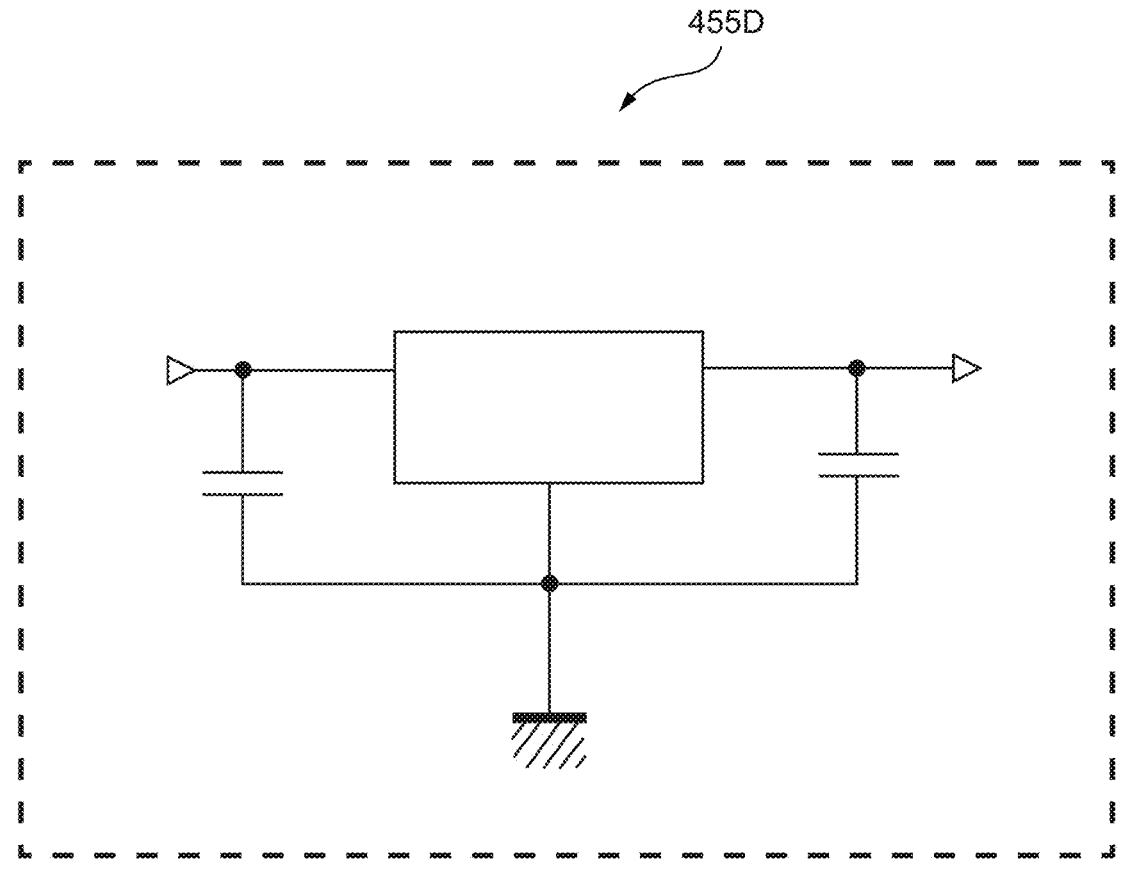
Figure 4E:
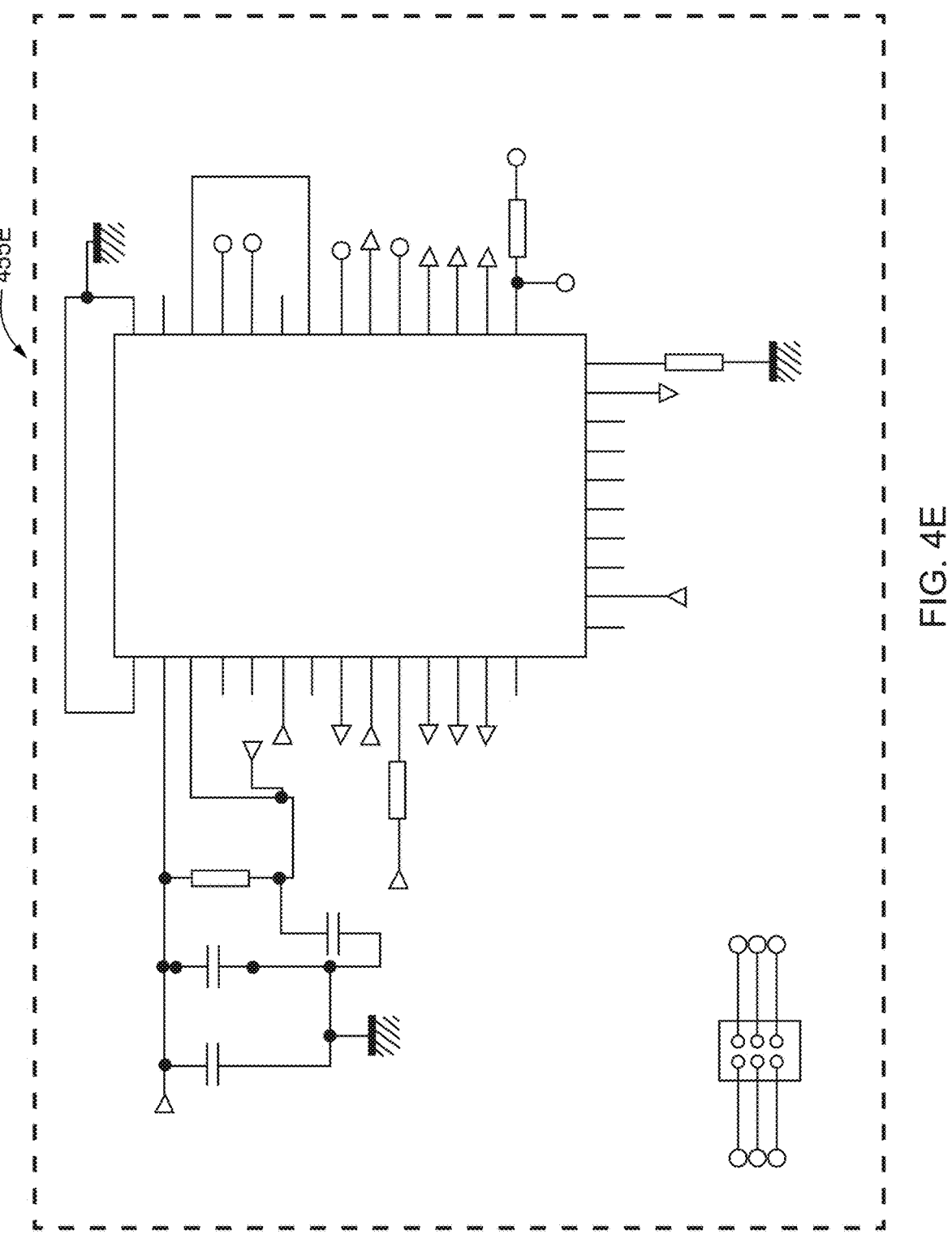

FIGS. 4A-4L show exemplary electronics components in accordance with various embodiments. FIG. 4A illustrates an exemplary load monitor circuit 455A that monitors an internal battery of a neurostimulator (e.g., neurostimulator 105 in FIG. 1). The load monitor circuit 455A manages the charging current as well as starts or stops the charging process depending on the voltage of the internal battery. FIG. 4B illustrates an exemplary on/off circuit 455B that energizes an input circuit of the neurostimulator to initiate functions programmed in the firmware. FIG. 4C illustrates an exemplary boost regulator DC/DC circuit 455C that raises and stabilizes battery voltage (e.g., 3.7 V) through a switching circuit to a voltage output (e.g., 5 V). The voltage is used to power the entire circuit. FIG. 4D illustrates an exemplary tension regulator circuit 455D that reduces the boost voltage (e.g., to 3.3 V) for microcontroller operation. FIG. 4E illustrates an exemplary processing circuit 455E that processes data and performs programmed functions. For example, the processing circuit 455E can receive a signal from a sensor (e.g., sensors 210 in FIG. 10), send stimulation signals, and monitor processes of the complementary circuits.

Figure 4F:
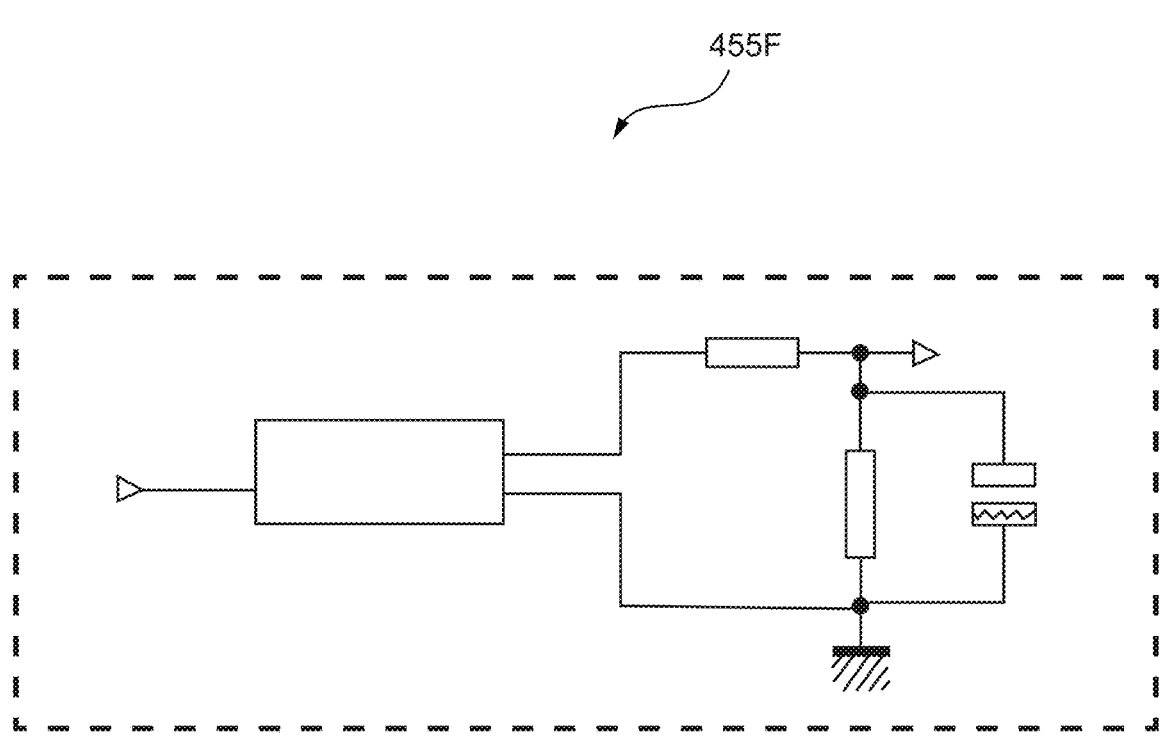
Figure 4G:
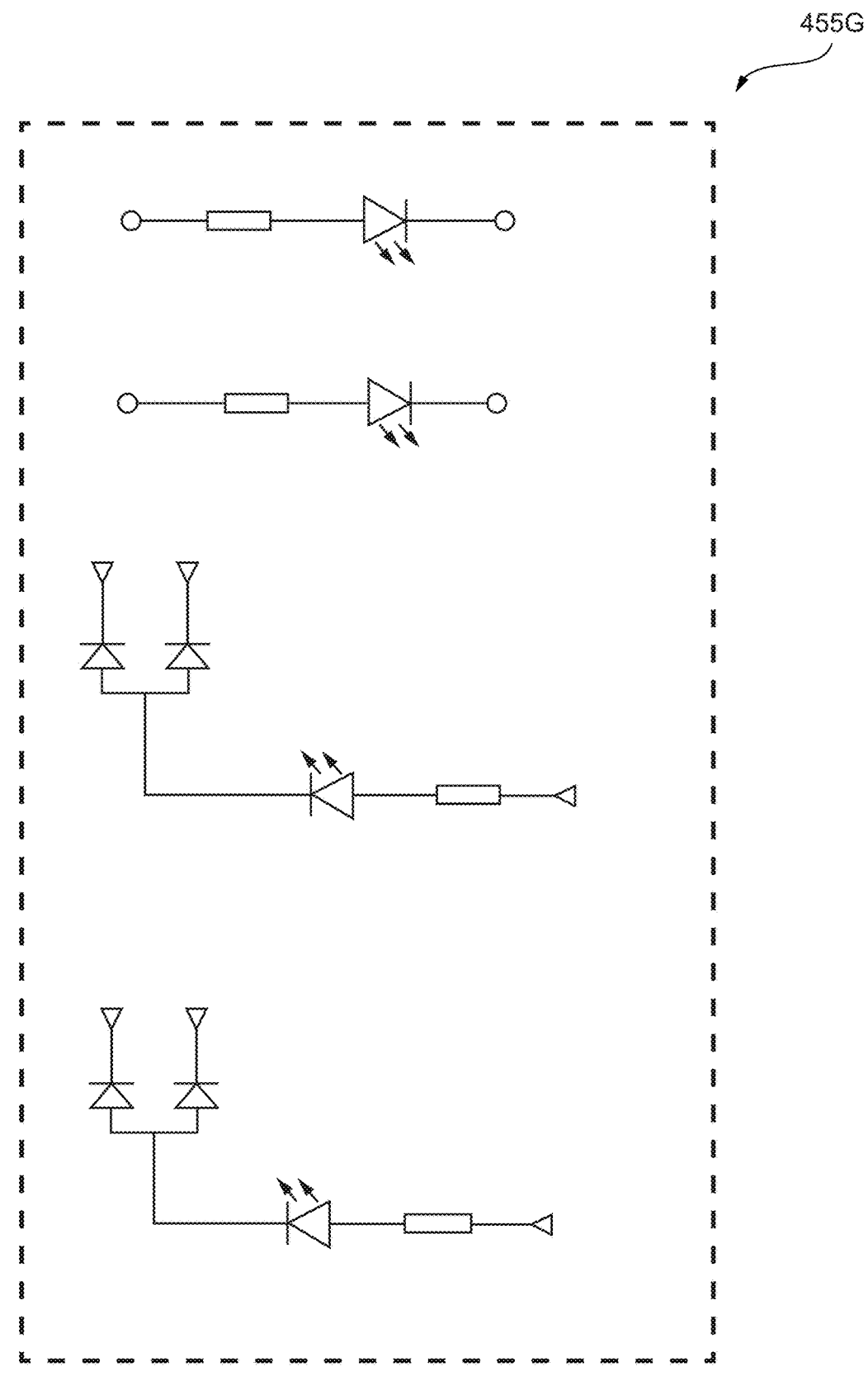
Figure 4H:
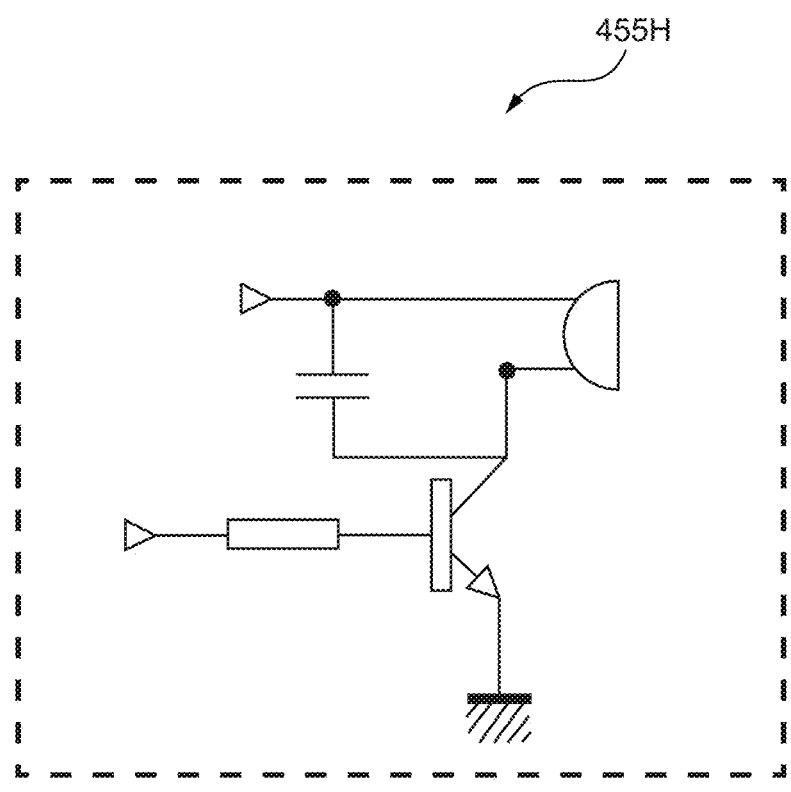
Figure 4I:
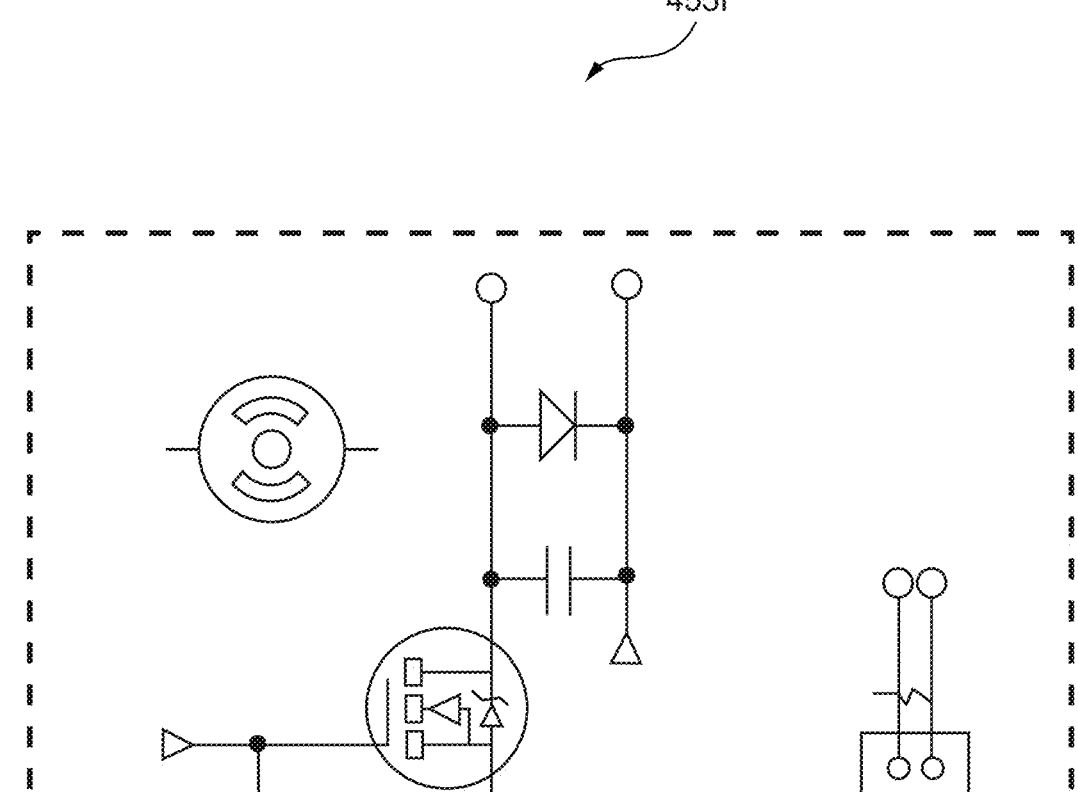
Figure 4J:
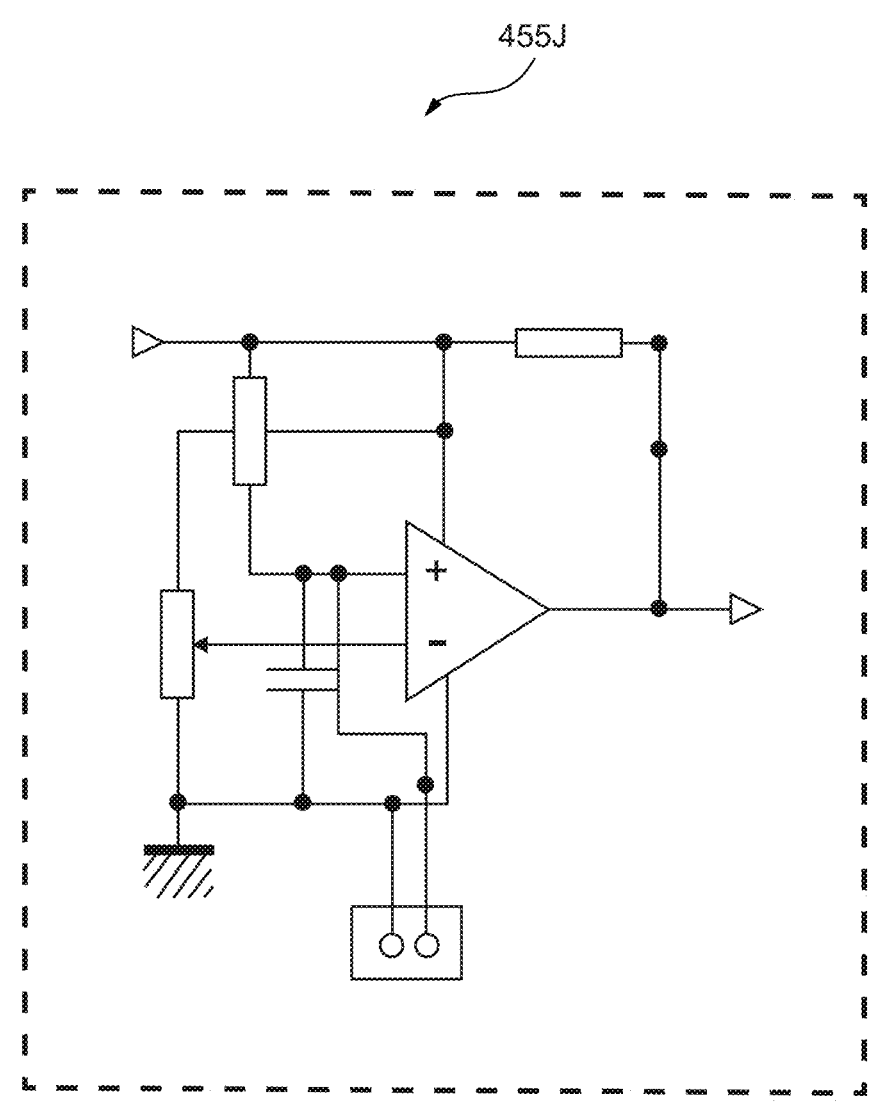
Figure 4K:
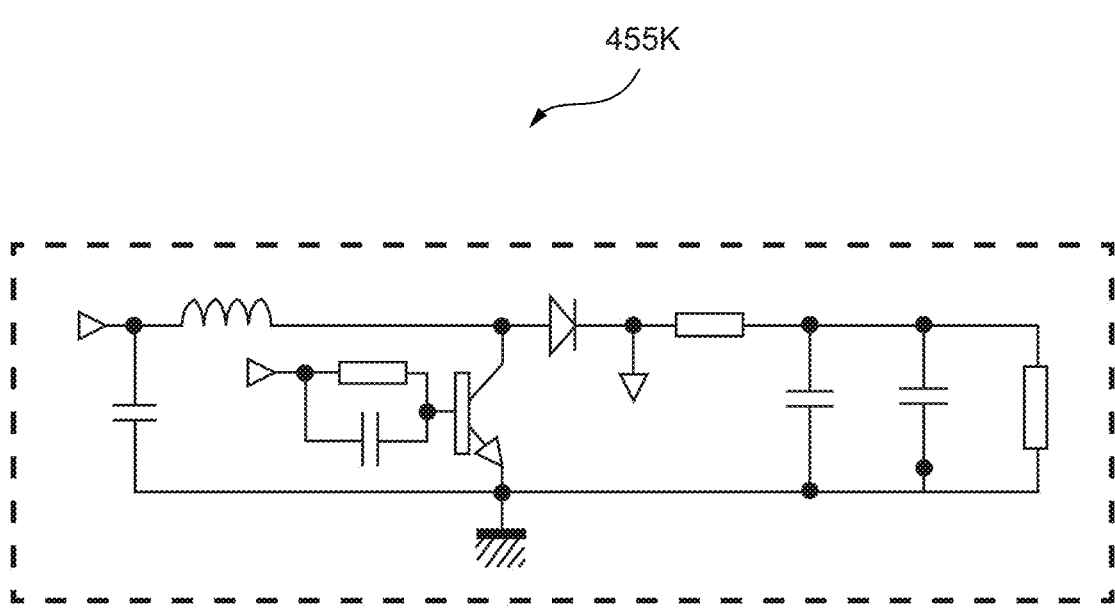
Figure 4L:
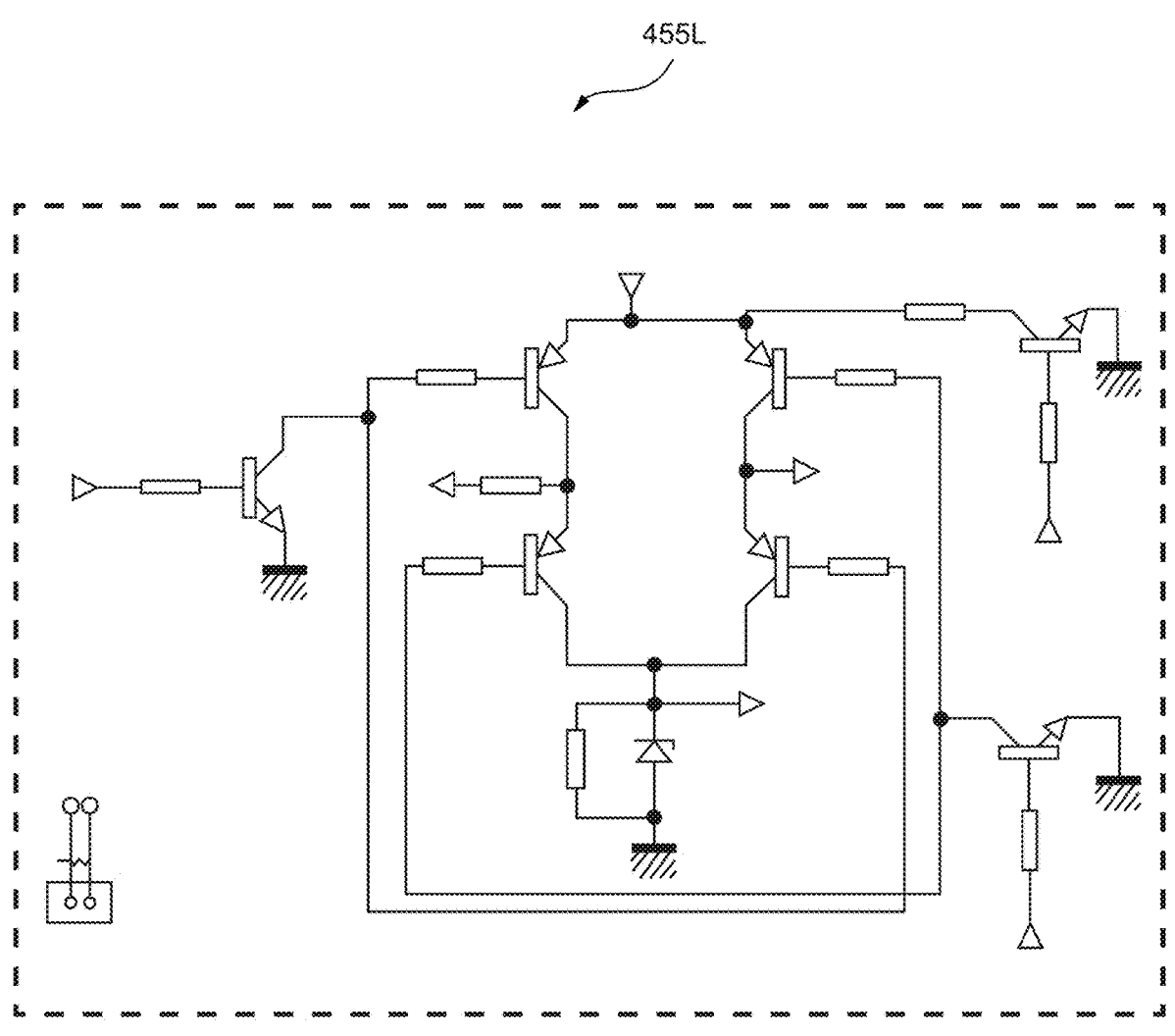

FIG. 4F illustrates an exemplary charge monitor circuit 455F that sends an analog signal to a microcontroller with the battery voltage information. A voltage supervisor resets the signal when the battery is less than or equal to a cut-off voltage. FIG. 4G illustrates an exemplary LED circuit 455G that signals a status of the neurostimulator. For instance, green can indicate that the neurostimulator is connected and charged, yellow can indicate an alert or an error, blue can indicate Bluetooth connectivity, and orange can indicate low battery or charging. FIG. 4H illustrates an alarm circuit 455H that emits programmed sounds through a buzzer. FIG. 4I illustrates an exemplary vibration circuit 455I that vibrates the neurostimulator through a motor that is triggered by the microcontroller. FIG. 4J illustrates an exemplary sensor monitor circuit 455J that monitors the sensor through a voltage comparator circuit that, when activates, changes the logic state sent to the microcontroller, indicating that there is moisture in the sensor. FIG. 4K illustrates an exemplary DC-DC converter circuit 455K that amplifies and stabilizes the input voltage, while keeping the output signal without oscillations through a linear control of the supply voltage, which is performed by means of switching. FIG. 4L illustrates an exemplary inverter circuit 455L that switches the direction in which current flows in the electrodes (e.g., electrodes 220 in FIG. 2). The switching can occur at a preprogrammed frequency, such as 2500 Hz with a burst of 50 Hz.

IV. Techniques for Delivering Neuromodulation

Figure 5:
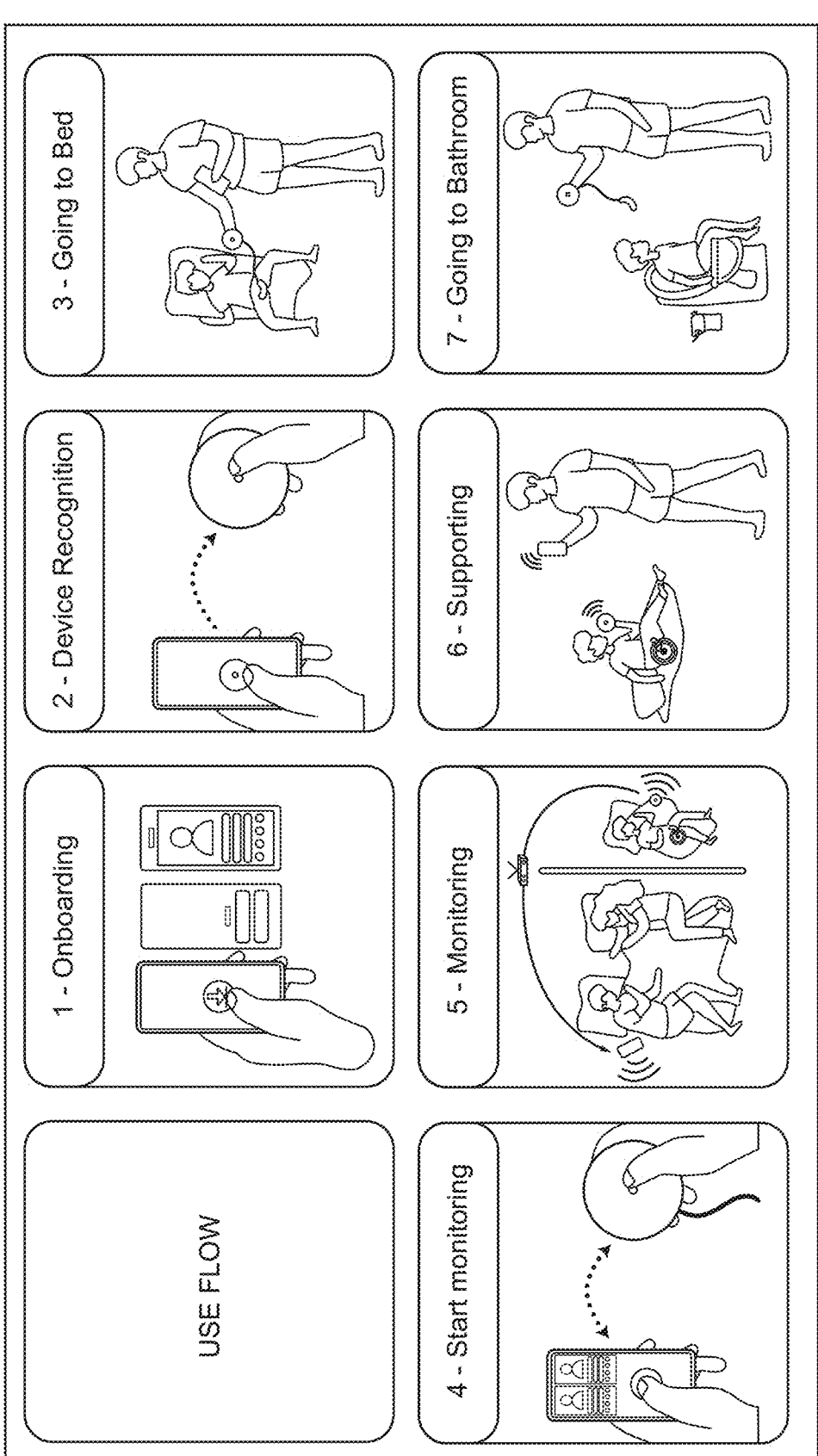
FIG. 5 shows an exemplary flow of providing neurostimulation in accordance with various embodiments.

FIG. 5 depicts a simplified flow depicting processing performed for delivering neuromodulation according to various embodiments. As noted herein, the flow of FIG. 5 illustrates the architecture, functionality, and operation of possible implementations of systems, methods, and computer program products according to various embodiments. In this regard, each block in the flow or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow illustration, and combination of blocks in the block diagrams and/or flow illustration, can be implemented by special purpose hardware-based systems that perform the specified functions or acts, or combinations of special purpose hardware and computer instructions.

In FIG. 5, the flow begins with onboarding, which can involve installation of an application on a user device. In addition, a battery of a neurostimulator (e.g., neurostimulator 105 in FIG. 1) can be charged using a universal serial bus (USB) cable. A constant orange light can indicate that the neurostimulator is charging. A blinking green light can indicate that the battery is charged.

The flow can continue with device recognition by pairing the neurostimulator with the user device. The neurostimulator can be turned on by holding a power button for a certain amount of time (e.g., 3 seconds). A blinking blue light can indicate that Bluetooth of the neurostimulator is activated and waiting for a connection. A user can open the application, activate Bluetooth, and connect to the neurostimulator. A constant blue light can indicate that the neurostimulator is in a configuration mode and can be configured. From the application, the user can select a pulse intensity and monitoring mode (e.g., Wi-Fi or Bluetooth).

The flow can continue with an end user going to bed. To prepare the neurostimulator, gel pads can be attached to electrodes of the neurostimulator. Another gel pad can be attached to a pad of the neurostimulator. An absorbent pad can also be attached to a sensor of the neurostimulator. Liners can be removed from the gel pads and absorbent pad so that the gel pads can be placed onto the neurostimulator. Additional liners may be peeled from the gel pads so that the gel pads can be placed on the end user. A gel pad for body fixation can be placed low on the pubic bone area. The stimulation electrodes can be on the pelvic floor area.

The flow can continue with the neurostimulator starting monitoring. To start monitoring, the neurostimulator can be turned on. From the application, a user can choose the pulse intensity and the monitoring mode. For Bluetooth, the user device may need to remain within a certain distance (e.g., 30 feet) of the neurostimulator. The application then begins monitoring and a green light on the neurostimulator indicates that the monitoring was started correctly.

At some point during the monitoring, an enuresis event can be detected. When the sensor gets wet, the neurostimulator applies an electrical pulse and activate an enuresis alert. As a result, the end user can wake up and remove the neurostimulator to urinate. The enuresis alert can be indicated by a constant yellow light (e.g., the indicator 250), an intermittent sound (e.g., beep) emitted by the neurostimulator, a vibration signal emitted by the neurostimulator, or a combination thereof. The electrical pulse can be set to go off after a predetermined amount of time (e.g., 5 seconds). In contrast, the enuresis alert may only go off after a button press For example, to deactivate the enuresis alert, the neurostimulator can be turned off by holding the button on the neurostimulator for a certain period of time (e.g., 10 seconds or after 3 beeps). Additionally or alternatively, the enuresis alert can deactivated using the application. If needed, the sound and vibration signals of the neurostimulator can be paused for a period of time (e.g., 5 minutes) by pressing the button for less than the certain period of time. After the period of time, the alerts are reactivated. The user may alternatively pause the sound and vibration signals on the neurostimulator for the period of time using the application.

In addition or alternative to the enuresis alert, an enuresis alert notification can be sent (e.g., using WiFi, Bluetooth, or the like) to the user device (e.g., a cellphone), which can alert the end user (e.g., adolescent or young adult) or a caregiver to wake up and help the end user if desired. The enuresis alert notification can be a push notification associated with the application and can be transmitted in response to the enuresis even being detected. The enuresis alert notification may cause an audible alert or vibration signal at the user device to cause the user or caregiver to wake up. In this way, the caregiver does not have to be with (e.g., in the same room as) the end user to wake up and help.

Once the end user, and optionally a caretaker, is awake, the absorbent pad and the gel pads can be changed if needed. To change the absorbent pad, when the neurostimulator is off, the electrodes pad can be removed from the end user. The absorbent pad can then be removed and replaced with a new one. The absorbent pad can be discarded. The gel pads can also be changed if needed. The electrode pads can then be replaced on the end user's skin and the neurostimulator can be turned on to restart the monitoring.

When monitoring is finished, the neurostimulator can be turned off by holding the button. The electrode pads can be removed from the end user. The absorbent pad can then be removed and discarded. Liners can be replaced over the gel pads. The neurostimulator can be cleaned, dried, and stored appropriately. At this point, the pulse intensity and monitoring mode may be adjusted.

FIG. 6 shows an exemplary flowchart of providing neurostimulation in accordance with various embodiments. As noted herein, the flowchart of FIG. 6 illustrates the architecture, functionality, and operation of possible implementations of systems, methods, and computer program products according to various embodiments. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flow illustration, can be implemented by special purpose hardware-based systems that perform the specified functions or acts, or combinations of special purpose hardware and computer instructions.

At block 605, a triggering event for neural stimulation is detected. The triggering event may be a detection of moisture by one or more sensors of a medical device. The one or more sensors can be moisture or humidity sensors embedded in a pad worn by a user. The pad can also include one or more electrodes in contact with a pelvic floor region of the user. Gel pads may be placed over the electrodes to adhere the pad to the pelvic floor region. In addition, the medical device can include a TENS device with a controller in communication with the sensors and the electrodes without the use of wires.

At block 610, the neural stimulation is provided by the one or more electrodes to the pelvic floor region of the user. The neural stimulation can be activated by the detection of the triggering event. The neural stimulation can include a current frequency (e.g., 2400 Hz), one or more waveform parameters (e.g., a Russian wave current) based on a motor threshold of the subject, and a current intensity based on an interval between bursts of the current frequency. Since a sensory threshold of the user is not reached by the medical device, a healthcare professional may not be needed to calibrate the medical device to the user.

At block 615, the neural stimulation causes muscular contraction of the pelvic floor region to occlude a urethra of the user and prevent urinary loss. In addition to occluding the urethra, the muscular contraction of the pelvic floor region can also inhibit contraction of the bladder by reflex, further preventing urinary loss. The medical device may additionally output an alarm, or may cause a user device in communication with the medical device to output an alarm indicating the detection of the triggering event. Additional vibration stimulation may also be provided to the user by the medical device in response to detecting the triggering event.

V. Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed:

1. A medical device comprising:
   a transcutaneous electrical nerve stimulation (TENS) device comprising an electronics module comprising: a controller configured to provide a set of stimulation parameters, and a pulse generator configured to generate neural stimulation based on the set of stimulation parameters;
   two or more electrodes connected to the TENS device for delivering the neural stimulation generated by the pulse generator to a perineal region of a user;

one or more gel pads for adhering the one or more electrodes to the perineal region of the user;

one or more sensors for detecting a triggering event for the neural stimulation; and a pad attached to the TENS device, the one or more electrodes, the one or more sensors, and the one or more gel pads, the pad comprising a first section attached to a sensor of the one or more sensors, a second section attached to a first electrode of the two or more electrodes, and a third section attached to a second electrode of the two or more electrodes, wherein the second section and the third section are attached to and extend from the first section.

2. The medical device of claim 1, further comprising:

a body fixation pad attached to the pad for adhering the pad to a pubic bone region of the user.

3. The medical device of claim 1, wherein the TENS device further comprises a light indicator for indicating a status of the TENS device.

4. The medical device of claim 1, wherein the TENS device is configured to be communicatively coupled to a user device.

5. The medical device of claim 4, wherein the user device is configured to send an indication of the set of stimulation parameters to the controller.

6. The medical device of claim 4, wherein the TENS device is configured to trigger an output of an alarm at the user device based on detecting the triggering event.

7. The medical device of claim 1, wherein the triggering event is an enuresis event and the one or more sensors are humidity or moisture sensors.

8. The medical device of claim 1, wherein the set of stimulation parameters include a frequency, an intensity, a duration, and a waveform.

9. The medical device of claim 8, wherein the frequency is between 1500 Hz and 2500 Hz.

10. The medical device of claim 8, wherein the waveform is a Russian wave current.

11. A computer-implemented method comprising:

detecting, by a sensor embedded in a pad of a medical device, a triggering event for neural stimulation, the pad comprising a first section attached to the sensor, a second section attached to a first electrode of two or more electrodes, and a third section attached to a second electrode of the two or more electrodes, wherein the second section and the third section are attached to and extend from the first section;

in response to detecting the triggering event, providing, by the two or more electrodes attached to the pad of the medical device and contacting a pelvic floor region of a user, the neural stimulation to the pelvic floor region, the neural stimulation comprising a current frequency, one or more waveform parameters based on a motor threshold of the user, and a current intensity based on an interval between bursts of the current frequency; and causing, by the neural stimulation, muscular contraction of the pelvic floor region to occlude a urethra of the user and prevent urinary loss.

12. The computer-implemented method of claim 11, wherein the one or more waveform parameters comprise a Russian wave current.

13. The computer-implemented method of claim 11, wherein the current frequency is between 1500 Hz and 2500 Hz.

14. The computer-implemented method of claim 11, further comprising:

in response to detecting the triggering event, outputting an alarm.

15. The computer-implemented method of claim 14, wherein the alarm is output by a user device communicatively coupled to the medical device.

16. The computer-implemented method of claim 11, wherein the medical device comprises:

a transcutaneous electrical nerve stimulation (TENS) device comprising an electronics module comprising: a controller configured to provide a set of stimulation parameters, and a pulse generator configured to generate the neural stimulation based on the set of stimulation parameters;

the two or more electrodes connected to the TENS device for delivering the neural stimulation generated by the pulse generator to the pelvic floor region of the user;

one or more gel pads for adhering the two or more electrodes to the pelvic floor region of the user; and the pad attached to the TENS device, the two or more electrodes, the sensor, and the one or more gel pads.

17. A transcutaneous electrical nerve stimulation (TENS) device comprising:

an electronics module comprising a controller configured to provide a set of stimulation parameters; and a pulse generator configured to generate neural stimulation based on the set of stimulation parameters and in response to one or more sensors detecting a triggering event for the neural stimulation, wherein the TENS device is connected to two or more electrodes configured to deliver the neural stimulation generated by the pulse generator to a perineal region of a user, wherein the two or more electrodes are adhered to the perineal region of the user via one or more gel pads, wherein the TENS device, the two or more electrodes, the one or more sensors, and the one or more gel pads are attached to a pad, the pad comprising a first section attached to a sensor of the one or more sensors, a second section attached to a first electrode of the two or more electrodes, and a third section attached to a second electrode of the two or more electrodes, wherein the second section and the third section are attached to and extend from the first section.

18. The TENS device of claim 17, further comprising a light indicator for indicating a status of the TENS device.

19. The TENS device of claim 17, wherein the TENS device is communicatively coupled to a user device.

* * * * *